(12) United States Patent
Koiso

(10) Patent No.: US 11,344,401 B2
(45) Date of Patent: *May 31, 2022

(54) IN-VIVO INDWELLING TUBE

(71) Applicant: KANEKA CORPORATION, Osaka (JP)

(72) Inventor: Tomoharu Koiso, Settsu (JP)

(73) Assignee: KANEKA CORPORATION, Osaka (JP)

( * ) Notice: Subject to any disclaimer, the term of this patent is extended or adjusted under 35 U.S.C. 154(b) by 264 days.

This patent is subject to a terminal disclaimer.

(21) Appl. No.: 16/616,303

(22) PCT Filed: Jun. 7, 2018

(86) PCT No.: PCT/JP2018/021864
§ 371 (c)(1),
(2) Date: Nov. 22, 2019

(87) PCT Pub. No.: WO2018/230435
PCT Pub. Date: Dec. 20, 2018

(65) Prior Publication Data
US 2021/0161640 A1 Jun. 3, 2021

(30) Foreign Application Priority Data

Jun. 13, 2017 (JP) .............................. JP2017-115570

(51) Int. Cl.
*A61F 2/04* (2013.01)
*A61F 2/95* (2013.01)

(52) U.S. Cl.
CPC .................. *A61F 2/04* (2013.01); *A61F 2/95* (2013.01); *A61F 2002/041* (2013.01)

(58) Field of Classification Search
CPC ..... A61F 2/07; A61F 2/95; A61F 2/84; A61B 2018/00535

(Continued)

(56) References Cited

U.S. PATENT DOCUMENTS

| | | | |
|---|---|---|---|
| 5,282,860 A | 2/1994 | Matsuno et al. | |
| 8,221,505 B2 * | 7/2012 | Skerven | A61F 2/2476 623/23.68 |

(Continued)

FOREIGN PATENT DOCUMENTS

| | | |
|---|---|---|
| JP | 62-72375 A | 4/1987 |
| JP | 1-152636 U | 10/1989 |

(Continued)

OTHER PUBLICATIONS

International Search Report (PCT/ISA/210) issued in PCT/JP2018/021864, dated Sep. 4, 2018.

(Continued)

*Primary Examiner* — Suzette J Gherbi
(74) *Attorney, Agent, or Firm* — Birch, Stewart, Kolasch & Birch, LLP

(57) ABSTRACT

Provided is an in-vivo indwelling tube having a high flap strength and passing smoothly through a conduit of an endoscope. A tubular member having a proximal side and a distal side; a proximal flap, including a base end on a proximal side and a free end on a distal side, on the proximal side of the tubular member; and a distal flap, including a base end on a distal side and a free end on a proximal side, on the distal side of the tubular member are arranged; where the tubular member includes a distal side first supporting member provided on a distal side of a midpoint between the base end and the free end of the distal flap or a proximal side first supporting member provided on a proximal side of a midpoint between the base end and the free end of the proximal flap.

15 Claims, 15 Drawing Sheets

(58) Field of Classification Search
USPC .................................. 623/1.15, 23.64–23.68
See application file for complete search history.

(56) References Cited

U.S. PATENT DOCUMENTS

| | | | |
|---|---|---|---|
| 8,845,663 B2* | 9/2014 | Chmura | A61B 17/11 |
| | | | 606/153 |
| 9,095,457 B2* | 8/2015 | Gupta | A61F 2/04 |
| 9,585,742 B2* | 3/2017 | Nomura | A61F 2/82 |
| 10,849,771 B2* | 12/2020 | Harrison | A61F 2/95 |
| 2007/0005122 A1 | 1/2007 | Inoue | |
| 2008/0051911 A1 | 2/2008 | Rucker | |
| 2012/0330433 A1 | 12/2012 | Yamagata | |
| 2017/0080193 A1 | 3/2017 | Kamada | |
| 2017/0128188 A1* | 5/2017 | Nomura | A61F 2/04 |
| 2020/0170774 A1* | 6/2020 | Koiso | A61M 1/00 |
| 2020/0188149 A1* | 6/2020 | Amos | A61M 25/04 |
| 2021/0267778 A1* | 9/2021 | Sakai | A61F 2/848 |

FOREIGN PATENT DOCUMENTS

| | | |
|---|---|---|
| JP | 5-192389 A | 8/1993 |
| JP | 9-56809 A | 3/1997 |
| JP | 2001-224554 A | 8/2001 |
| JP | 2006-87712 A | 4/2006 |
| JP | 2015-36043 A | 2/2015 |
| WO | WO 2012/057313 A1 | 5/2012 |
| WO | WO 2015/133333 A1 | 9/2015 |

OTHER PUBLICATIONS

Written Opinion (PCT/ISA/237) issued in PCT/JP2018/021864, dated Sep. 4, 2018.

* cited by examiner

【Fig. 1】
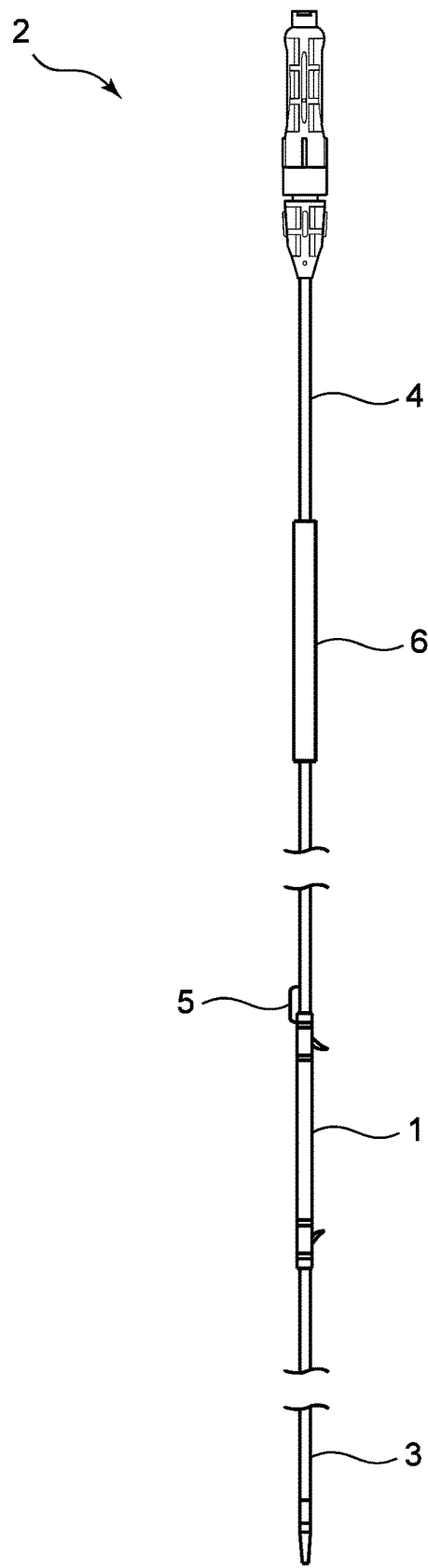

[Fig. 2]
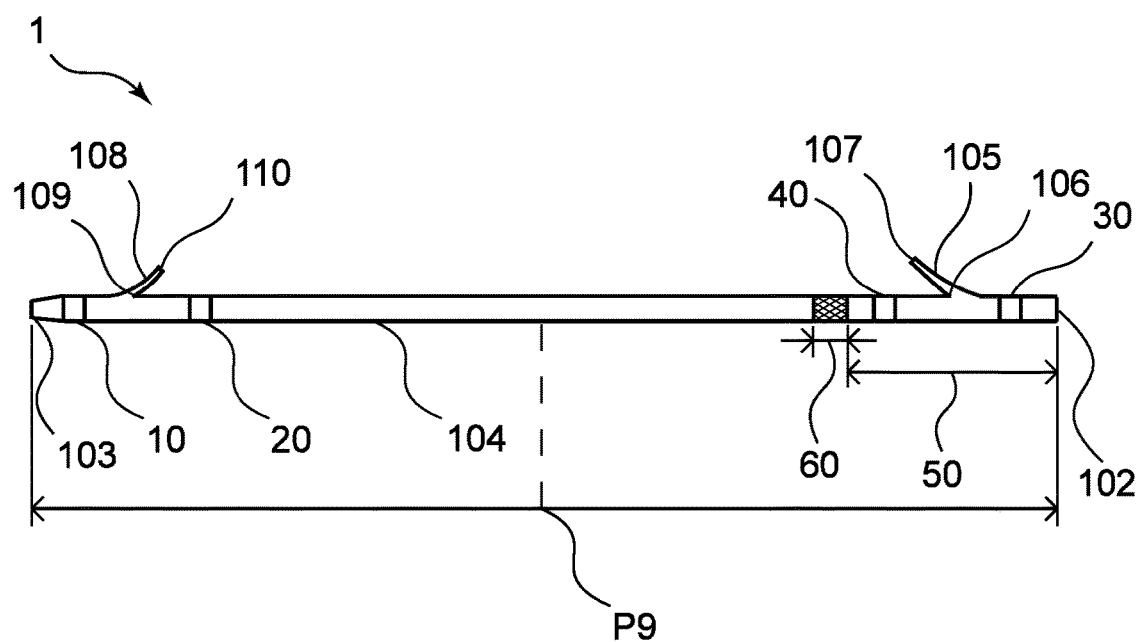

[Fig. 3]
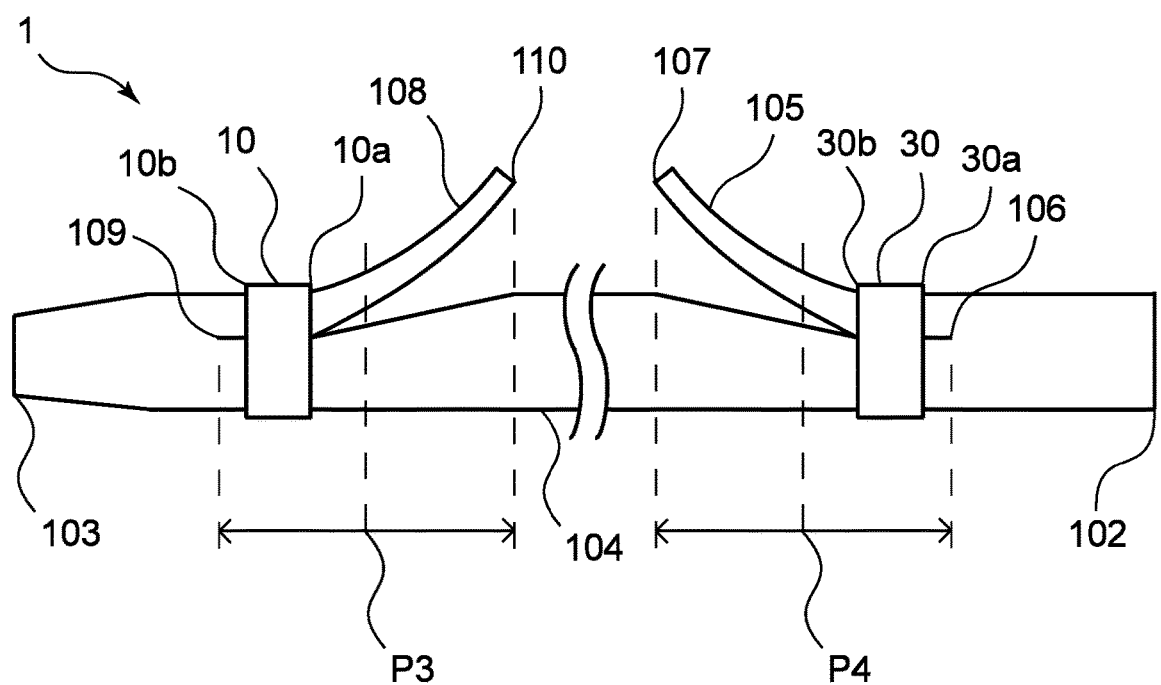

[Fig. 4]
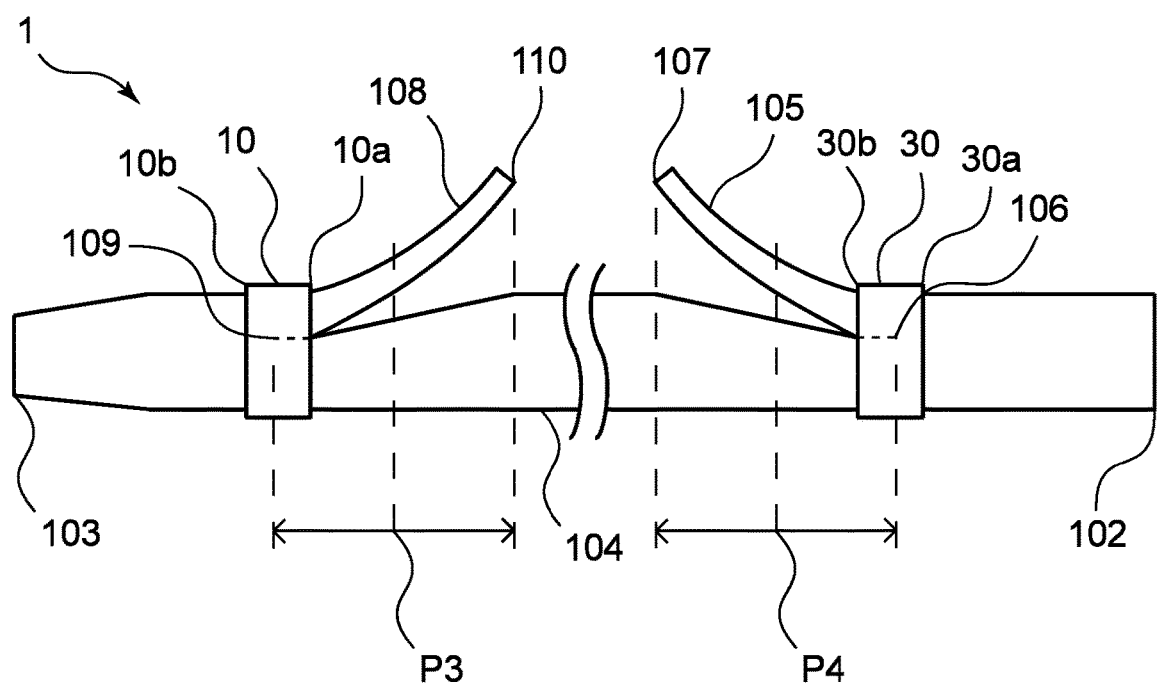

[Fig. 5]
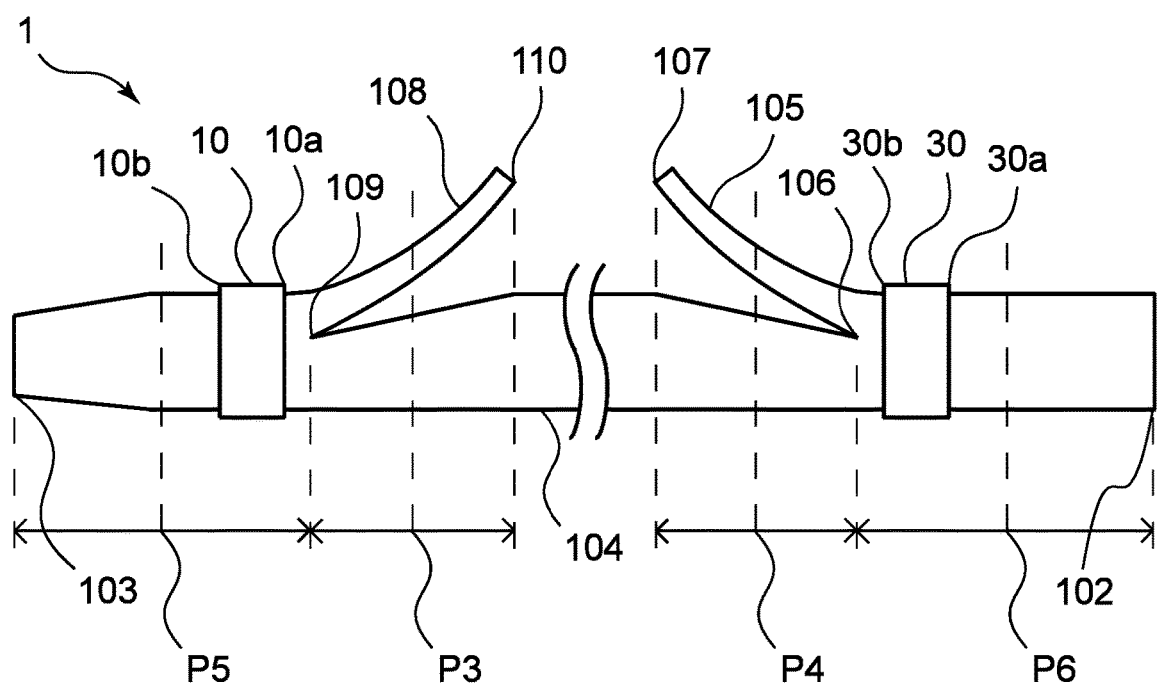

[Fig. 6]
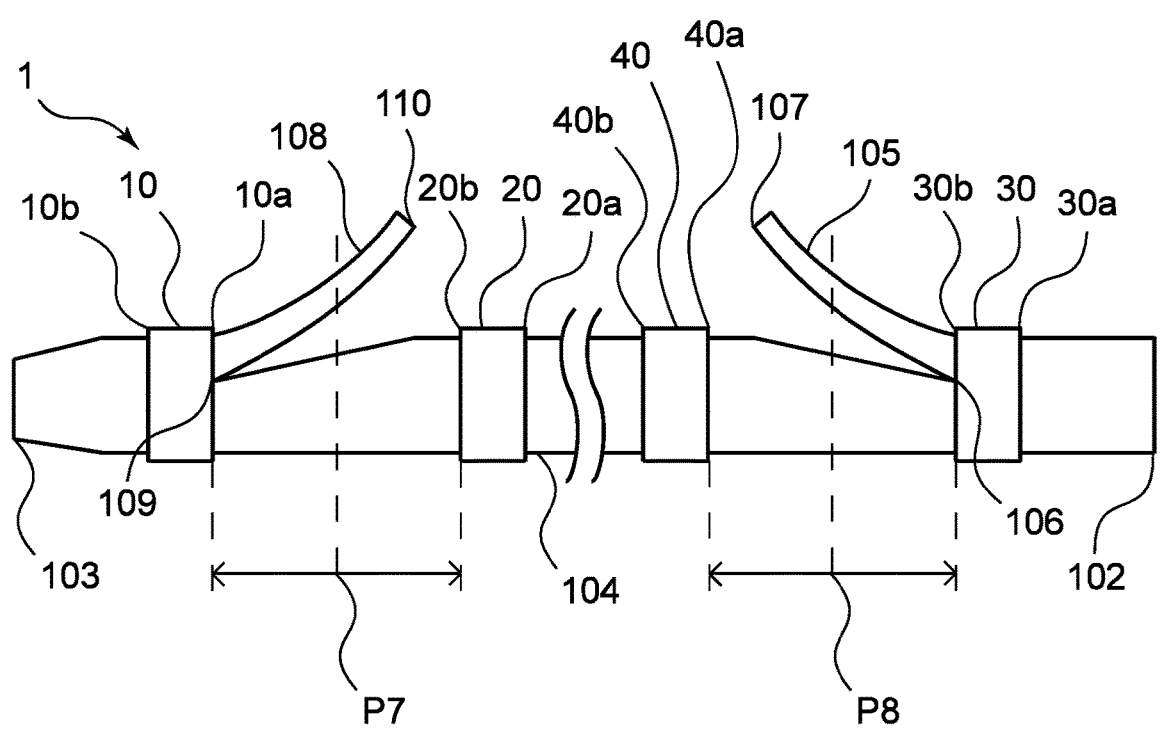

[Fig. 7]
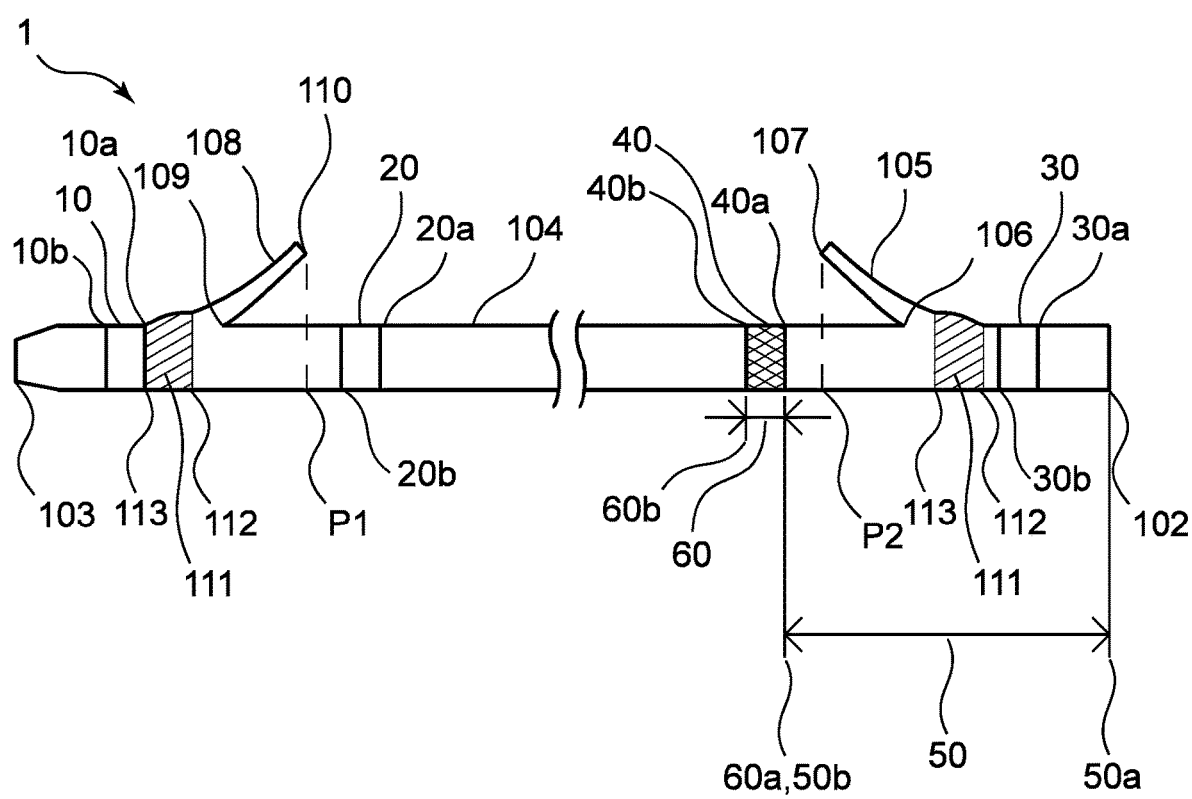

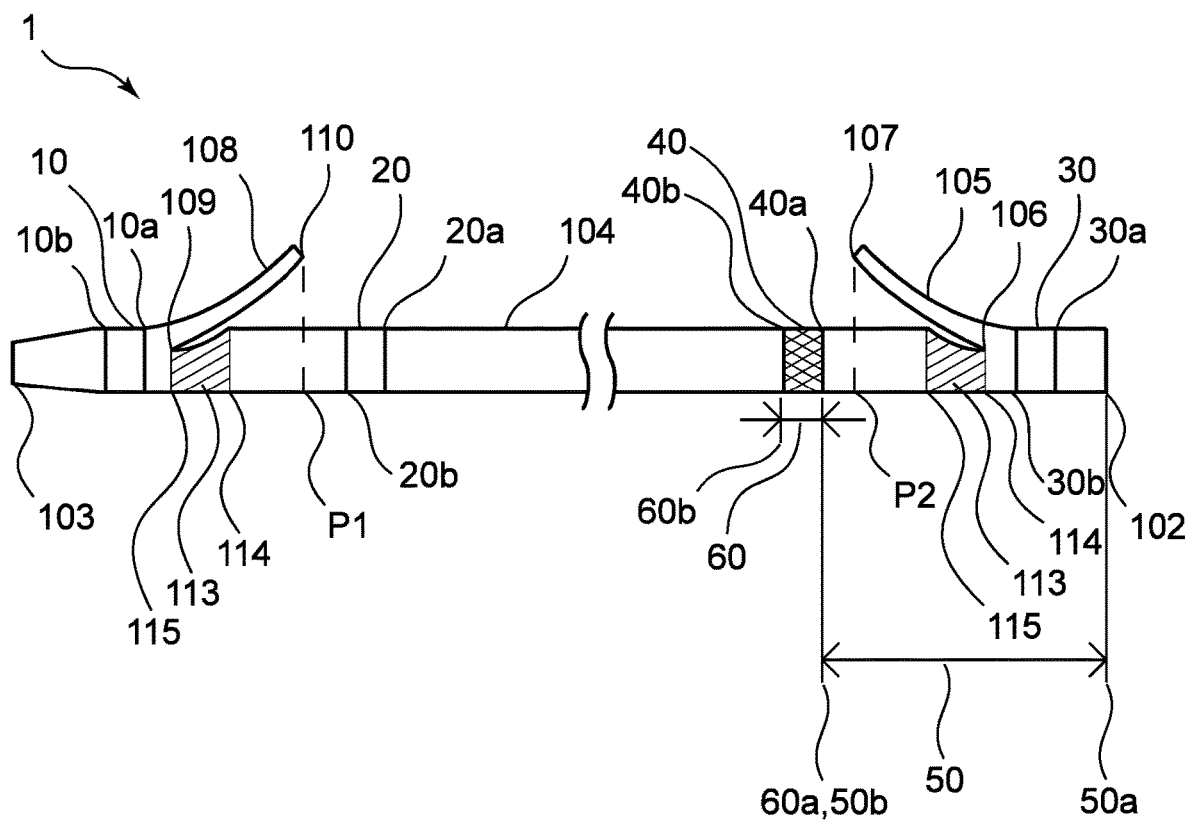
[Fig. 8]

[Fig. 9]
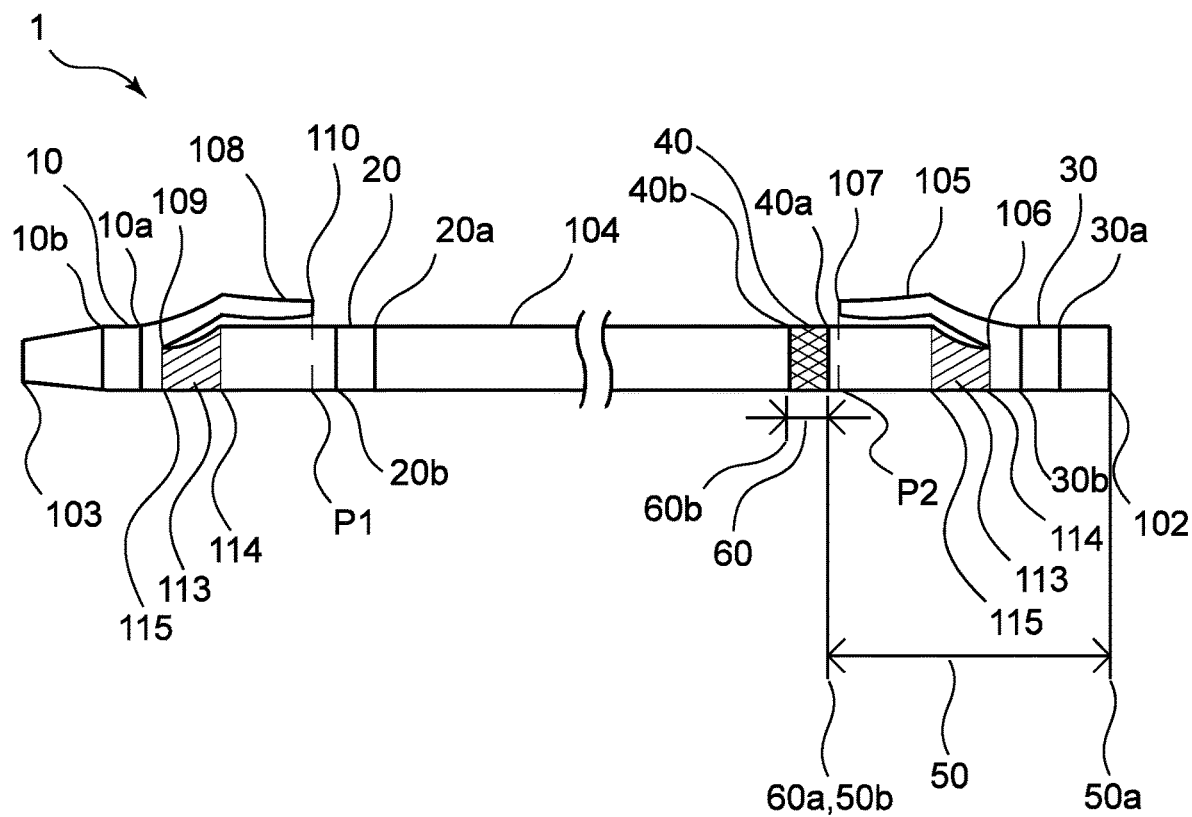

[Fig. 10]
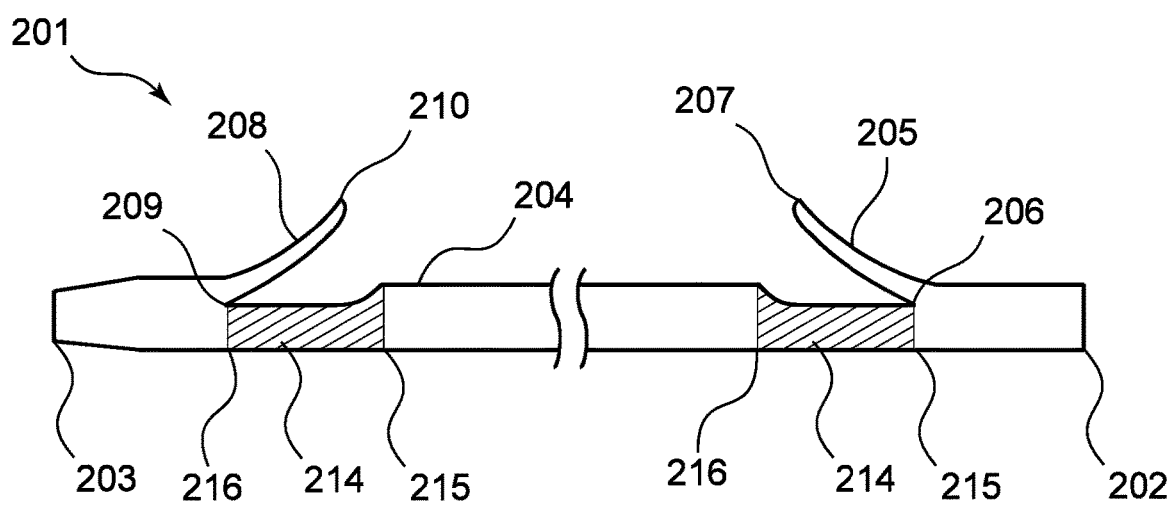

[Fig. 11]
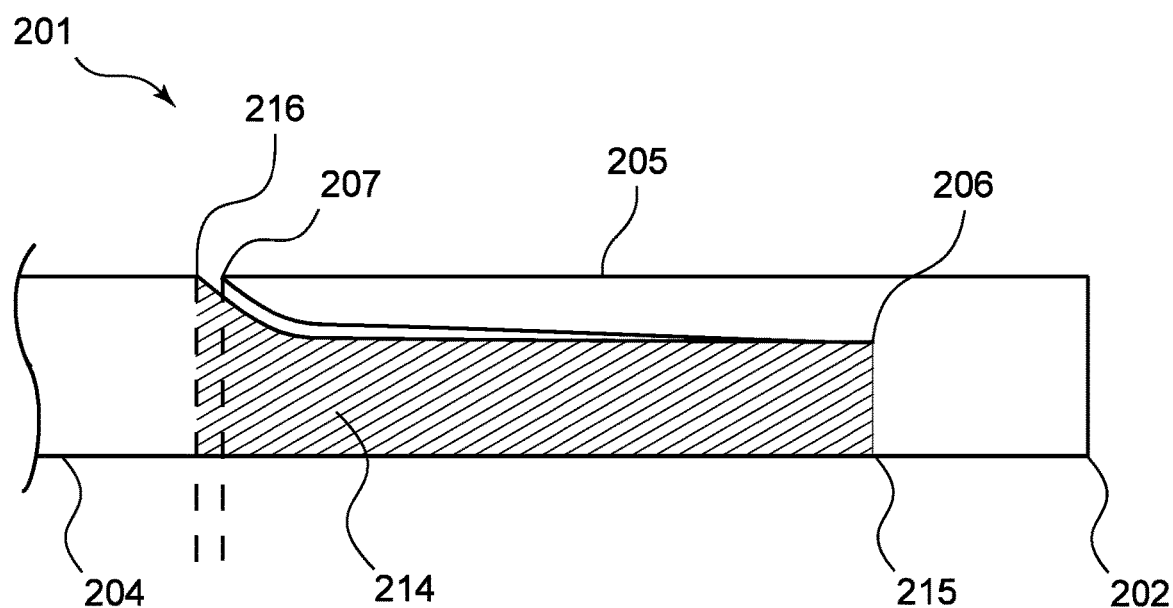

[Fig. 12]
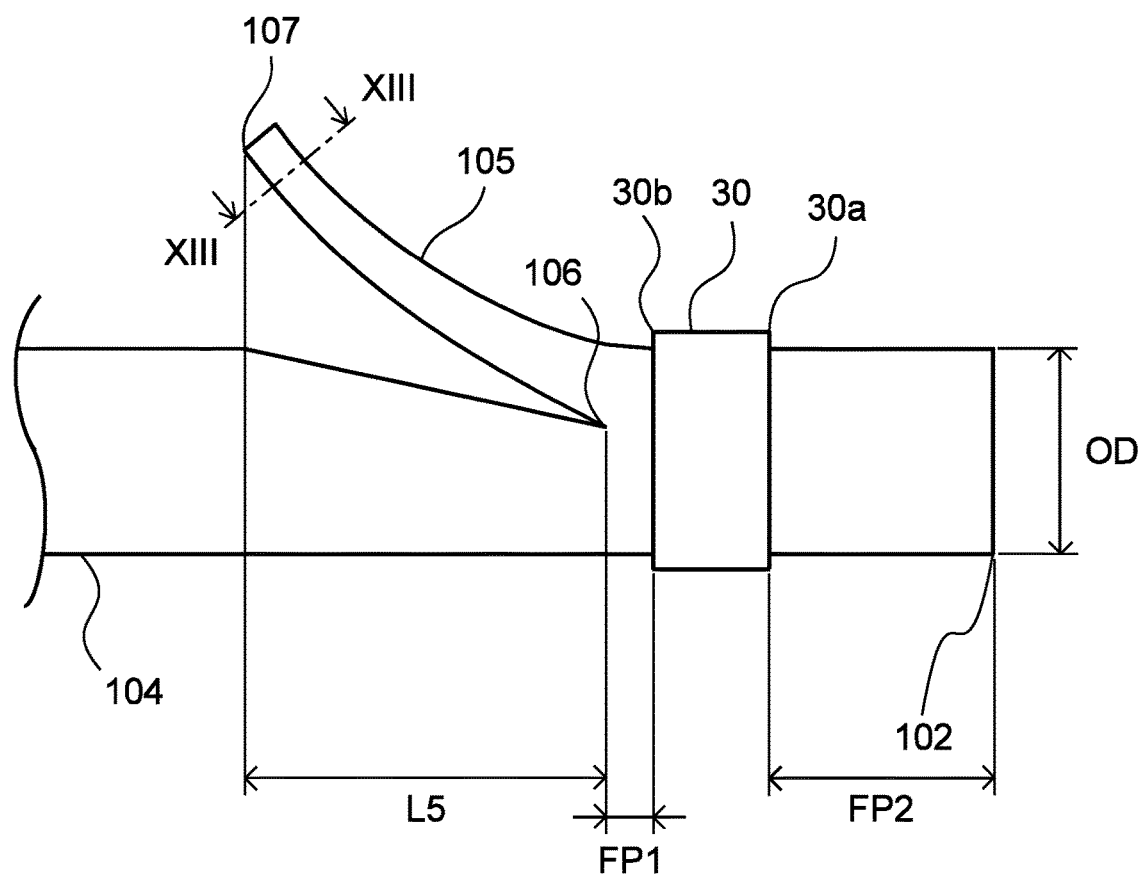

[Fig. 13]
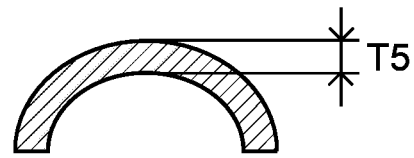

[Fig. 14]
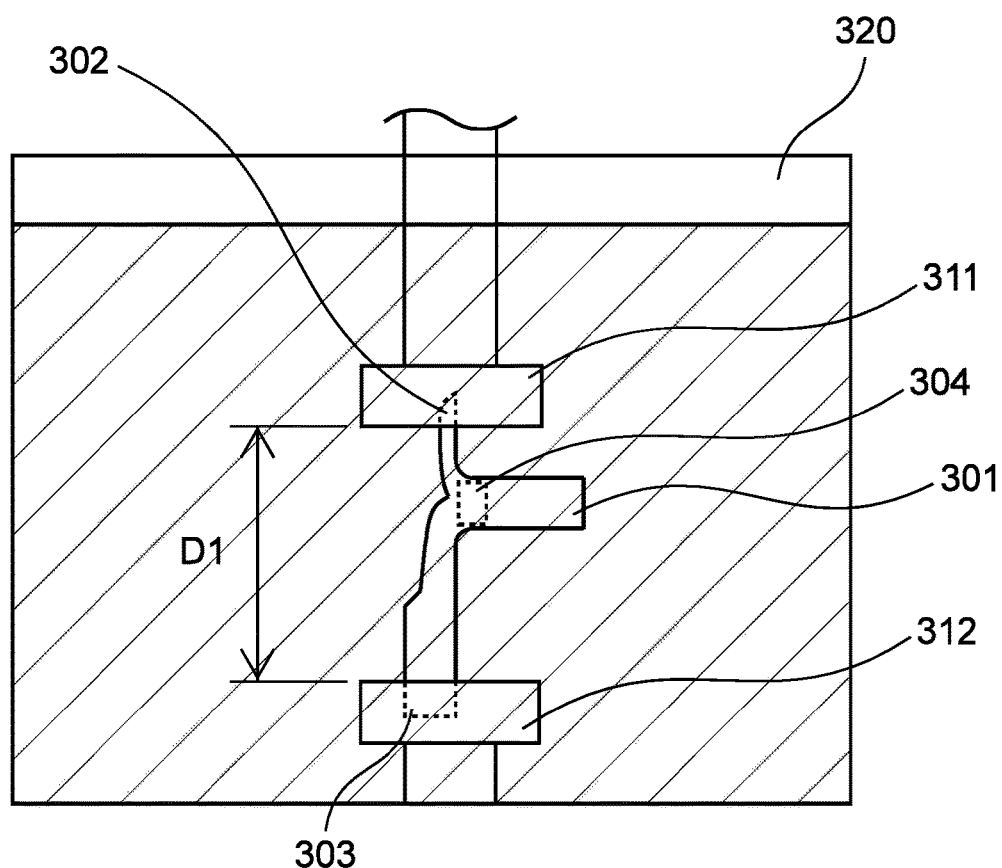

[Fig. 15]
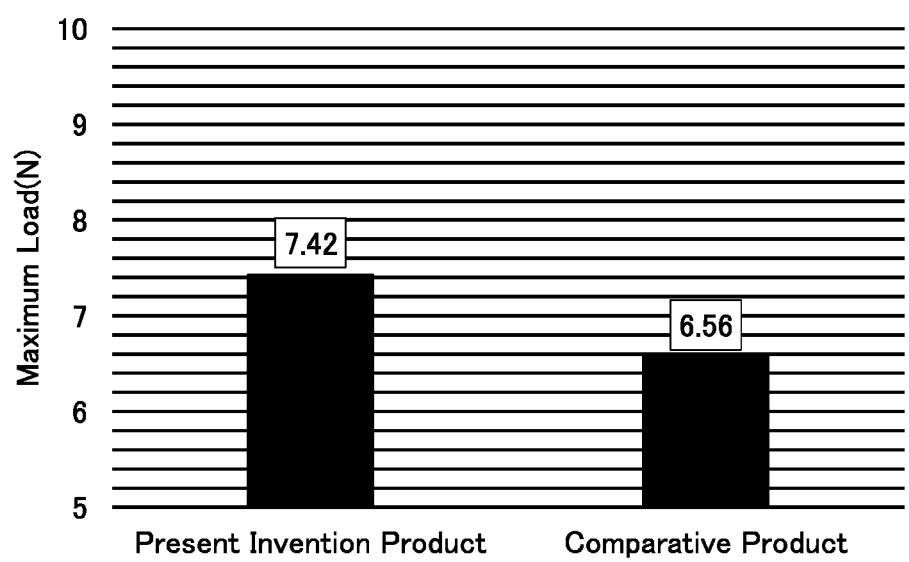

IN-VIVO INDWELLING TUBE

TECHNICAL FIELD

The present invention relates to an in-vivo indwelling tube having a flap.

BACKGROUND ART

An in-vivo indwelling tube represented by stents, particularly stents for bile ducts or pancreatic ducts are medical devices for treating various diseases such as biliary obstruction, jaundice, biliary tract cancer, and the like caused by constriction or occlusion of a lumen in the living body such as bile duct, pancreatic duct, and the like. The in-vivo indwelling tube is indwelled in the lumen in the living body for the purpose of draining bile from the bile duct to the duodenum and maintaining the inner diameter of the lumen by expanding the lesion at the constricted or occluded site from the inner side. When the tissue of a lesion such as a cancer cell enters the lumen of the in-vivo indwelling tube and the lumen of the in-vivo indwelling tube is occluded or constricted, the in-vivo indwelling tube needs to be replaced.

The in-vivo indwelling tube includes one made of a metal material and one made of a resin material. In the treatment as described above, an in-vivo indwelling tube made of a resin material may be used.

First, a conventional in-vivo indwelling tube will be described with reference to FIG. 10. As shown in FIG. 10, an in-vivo indwelling tube 201 made of a resin material includes a proximal end 202 and a distal end 203 and extends in a perspective direction. Generally, the in-vivo indwelling tube 201 has a cut on a proximal outer surface to form a proximal flap 205 and has a cut on a distal outer surface to form a distal flap 208 (e.g., Patent Documents 1 to 3). The proximal flap 205 and the distal flap 208 have the function of securing the in-vivo indwelling tube 201 in the lumen in the living body. When the in-vivo indwelling tube 201 is a bile duct stent, for example, the distal flap 208 is placed on the distal side than the constricted portion (occluded portion) of the bile duct so that the in-vivo indwelling tube does not fall off from the bile duct toward the duodenum side, and the proximal flap 205 is placed near the papilla of the duodenum so that the proximal end 202 of the in-vivo indwelling tube 201 does not penetrate into the bile duct.

PRIOR ART DOCUMENTS

Patent Documents

Patent Document 1: JP-A-2015-36043
Patent Document 2: JP-A-9-56809
Patent Document 3: JP-A-5-192389

SUMMARY OF THE INVENTION

Problems to be Solved by the Invention

In the in-vivo indwelling tube disclosed in Patent document 1 and Patent document 2, the outer periphery of a tubular member is axially cut to form a flap. However, such an in-vivo indwelling tube has problems in that the flap strength is low and the proximal end of the in-vivo indwelling tube cannot be sufficiently prevented from entering the bile duct or the like, and in that the flap is easily broken.

As disclosed in Patent document 3, if a reinforcement blade is arranged between the outer tube and the inner tube, the strength of not only the flap but also the entire in-vivo indwelling tube is enhanced. Therefore, such an in-vivo indwelling tube has problems in that it is difficult to pass the in-vivo indwelling tube through the conduit of the endoscope and that it is difficult to deliver the in-vivo indwelling tube to a desired indwelling site.

In view of the situations described above, it is an object of the present invention to provide an in-vivo indwelling tube having a high flap strength and capable of smoothing the passing through a conduit of an endoscope or the like.

Solutions to the Problems

An in-vivo indwelling tube of the present invention that has solved the above problems comprising: a tubular member having a proximal side and a distal side; a proximal flap, having a base end on a proximal side and a free end on a distal side, on the proximal side of the tubular member; and a distal flap, having a base end on a distal side and a free end on a proximal side, on the distal side of the tubular member, wherein the tubular member includes, radially outward of the tubular member, at least either a distal side first supporting member provided on a distal side of a midpoint between the base end and the free end of the distal flap or a proximal side first supporting member provided on a proximal side of a midpoint between the base end and the free end of the proximal flap.

The in-vivo indwelling tube is preferable wherein the tubular member satisfies at least either condition (1) or condition (2) below.

(1) The distal side first supporting member is provided on the proximal side of the base end of the distal flap.

(2) The proximal side first supporting member is provided on the distal side of the base end of the proximal flap.

The in-vivo indwelling tube is preferable wherein the tubular member satisfies at least either condition (1) or condition (2) below.

(1) The distal side first supporting member is provided over the base end of the distal flap.

(2) The proximal side first supporting member is provided over the base end of the proximal flap.

The in-vivo indwelling tube is preferable wherein the tubular member satisfies at least either condition (1) or condition (2) below.

(1) The distal side first supporting member is provided on a proximal side of a midpoint between the base end of the distal flap and the distal end of the tubular member.

(2) The proximal side first supporting member is provided on the distal side of a midpoint between the base end of the proximal flap and the proximal end of the tubular member.

The in-vivo indwelling tube is preferable wherein the tubular member included at least either a distal side second supporting member provided on the proximal side of the free end of the distal flap and on the distal side of a midpoint of the tubular member, or the proximal side second supporting member provided on the distal side of the free end of the proximal flap and on the proximal side of a midpoint of the tubular member.

The in-vivo indwelling tube is preferable wherein a midpoint between the proximal end of the distal side first supporting member and the distal end of the distal side second supporting member is on the distal side of the free end of the distal flap, and a midpoint between the distal end of the proximal side first supporting member and the proximal end of the proximal side second supporting member is on the proximal side of the free end of the proximal flap.

The in-vivo indwelling tube is preferable wherein the tubular member includes a first region and a second region sequentially from the proximal side of the tubular member, and colors of the first region and the second region differ from each other on the distal side of the base end of the proximal flap.

The in-vivo indwelling tube is preferable wherein the tubular member includes a larger diameter portion having a maximum outer diameter larger than an average outer diameter of the tubular member between a position of the tubular member corresponding to the free end of the distal flap or the proximal end of the distal side second supporting member, and a position of the tubular member corresponding to the free end of the proximal flap or the distal end of the first region, and the larger diameter portion on at least either the proximal side of the base end of the proximal flap or the distal side of the base end of the distal flap.

The in-vivo indwelling tube is preferable wherein the tubular member includes a smaller diameter portion having a minimum outer diameter smaller than an average outer diameter of the tubular member between the position of the tubular member corresponding to the free end of the distal flap or the proximal end of the distal side second supporting member and the position of the tubular member corresponding to the free end of the proximal flap or the distal end of the first region, and the smaller diameter portion is on at least either between the base end of the proximal flap and the position on the proximal side of the free end of the proximal flap when the proximal flap is in a closed state or between the base end of the distal flap and a position on the distal side of the free end of the distal flap when the distal flap is in a closed state.

The in-vivo indwelling tube is preferable wherein the tubular member has a hole in the smaller diameter portion.

The in-vivo indwelling tube is preferable wherein the tubular member includes at least one supporting member of the distal side first supporting member, a distal side second supporting member provided on the proximal side of the free end of the distal flap and on the distal side of a midpoint of the tubular member, the proximal side first supporting member, and a proximal side second supporting member provided on the distal side of the free end of the proximal flap and on the proximal side of a midpoint of the tubular member, and the shape of the at least one supporting member is tubular.

The in-vivo indwelling tube is preferable wherein the tubular member includes at least one supporting member of the distal side first supporting member, a distal side second supporting member provided on the proximal side of the free end of the distal flap and on the distal side of a midpoint of the tubular member, the proximal side first supporting member, and a proximal side second supporting member provided on the distal side of the free end of the proximal flap and on the proximal side of a midpoint of the tubular member, and the inner diameter of the at least one supporting member is smaller than the outer diameter of the tubular member.

The in-vivo indwelling tube is preferable wherein the tubular member includes at least one supporting member of the distal side first supporting member, a distal side second supporting member provided on the proximal side of the free end of the distal flap and on the distal side of a midpoint of the tubular member, the proximal side first supporting member, and a proximal side second supporting member provided on the distal side of the free end of the proximal flap and on the proximal side of a midpoint of the tubular member, and the material that constitutes the at least one supporting member is metal, or resin in which a type A durometer hardness of the material that constitutes the at least one supporting member is higher than a type A durometer hardness of the material that constitutes the tubular member.

Effects of the Invention

According to the present invention, the flap strength can be enhanced while maintaining the flexibility of the in-vivo indwelling tube itself.

BRIEF DESCRIPTION OF THE DRAWINGS

FIG. 1 shows a side view of a delivery system of an in-vivo indwelling tube according to an embodiment of the present invention.

FIG. 2 shows a side view of the in-vivo indwelling tube according to the embodiment of the present invention.

FIG. 3 shows an enlarged side view of an example in the vicinity of a distal flap of the in-vivo indwelling tube according to the embodiment of the present invention.

FIG. 4 shows an enlarged side view of another example in the vicinity of the distal flap of the in-vivo indwelling tube according to the embodiment of the present invention.

FIG. 5 shows an enlarged side view of another further example in the vicinity of the distal flap of the in-vivo indwelling tube according to the embodiment of the present invention.

FIG. 6 shows an enlarged side view of the vicinity of the distal flap of the in-vivo indwelling tube according to the embodiment of the present invention.

FIG. 7 shows a side view of an example of the in-vivo indwelling tube according to the embodiment of the present invention.

FIG. 8 shows a side view of another example of the in-vivo indwelling tube according to the embodiment of the present invention.

FIG. 9 shows a side view when a proximal flap is in a closed state of another example of the in-vivo indwelling tube according to the embodiment of the present invention.

FIG. 10 shows a side view of a conventional in-vivo indwelling tube.

FIG. 11 shows an enlarged side view in the vicinity of a proximal flap when the proximal flap is in a closed state of the conventional in-vivo indwelling tube.

FIG. 12 shows an enlarged side view of a flap portion of the in-vivo indwelling tube.

FIG. 13 shows a cross-sectional view taken along line XIII-XIII of the flap of the in-vivo indwelling tube shown in FIG. 12.

FIG. 14 shows an explanatory view on a measuring method of a tensile strength of a flap portion of a measurement sample.

FIG. 15 shows a graph of the measurement results of the tensile strength of the flap portion of the measurement sample.

MODE FOR CARRYING OUT THE INVENTION

Hereinafter, the present invention will be more specifically described based on the following embodiments, but the present invention is not limited by the following embodiments as a matter of course, and modifications can be appropriately made within a scope which can conform to the description made above and below, all of which being encompassed with in the technical scope of the present invention. In each drawing, hatching, member reference symbols, and the like are sometimes omitted for the sake of convenience, but in such a case, specification and other drawings are to be referred to. Furthermore, the dimensions of various members in the drawings may differ from the actual dimensions, as priority is given to helping to understand the features of the present invention.

The in-vivo indwelling tube is used by being attached to a delivery system (conveying device) such as a catheter having a site to install the in-vivo indwelling tube in order to convey the in-vivo indwelling tube to the lesion.

In the present invention, the proximal side refers to the direction on the hand side of the user (operator) with respect to the extending direction of the in-vivo indwelling tube, and the distal side refers to the direction opposite to the proximal side (that is, direction on treatment target side). In addition, the direction from the proximal side to the distal side of the in-vivo indwelling tube is referred to as an axial direction. The radial direction refers to the radius direction of the tubular member, inside in the radial direction refers to the direction toward the axial center side of the tubular member, and outside in the radial direction refers to the radial direction toward the side opposite side to the inner side.

In the following embodiments, the flap on the proximal side (proximal flap) and the flap on the distal side (distal flap) of the in-vivo indwelling tube may be collectively referred to as flaps. Furthermore, a distal side first supporting member and a proximal side first supporting member of the in-vivo indwelling tube may be collectively referred to as a first supporting member, and a distal side second supporting member and a proximal side second supporting member may be collectively referred to as a second supporting member. The first supporting member and the second supporting member may be collectively referred to as a supporting member. The distal side first supporting member and the distal side second supporting member may be collectively referred to as a distal side supporting member. The proximal side first supporting member and the proximal side second supporting member may be collectively referred to as a proximal side supporting member.

(1) Delivery System

Before describing the method for producing an in-vivo indwelling tube of the present invention in detail, a configuration example of a delivery system for delivering an in-vivo indwelling tube to an indwelling target site will be first described with reference to FIG. 1. An example of the delivery system is shown in FIG. 1. In the delivery system 2, an outer catheter 4 and the in-vivo indwelling tube 1 are placed on the outer side in the radial direction of the inner catheter 3. The in-vivo indwelling tube 1 and the outer catheter 4 are coupled by a suture thread 5. As the in-vivo indwelling tube 1 and the outer catheter 4 are coupled to each other, when being conveying to the lesion, the in-vivo indwelling tube 1 can be pulled back in the lumen in the living body to finely adjust the position. Therefore, the in-vivo indwelling tube 1 can be easily indwelled at an appropriate position of the lesion. The insertion auxiliary tube 6 is placed on the outer side in the radial direction of the outer catheter 4. The insertion auxiliary tube 6 can make it difficult for the flap to be folded back during conveyance of the in-vivo indwelling tube 1, and can prevent kinking of the delivery system 2 at the time of insertion. As a result, the in-vivo indwelling tube 1 can be conveyed smoothly.

(2) Overall Configuration of In-Vivo Indwelling Tube

In the present invention, the in-vivo indwelling tube includes a tubular member having a proximal side and a distal side, a proximal flap having a base end on a proximal side and a free end on a distal side on the proximal side of the tubular member, and a distal flap having a base end on a distal side and a free end on a proximal side on the distal side of the tubular member, and has a first supporting member provided radially outward of the tubular member on the distal side than a midpoint of the base end and the free end of the distal flap. Hereinafter, the in-vivo indwelling tube of the present invention will be described with reference to FIGS. 2 to 9. In FIGS. 2 to 9, the left direction in the plane of drawing corresponds to the distal side of the in-vivo indwelling tube, and the right direction in the plane of drawing corresponds to the proximal side of the in-vivo indwelling tube.

As shown in FIG. 2, the in-vivo indwelling tube 1 according to the embodiment of the present invention includes a tubular member 104 having a proximal side and a distal side, a proximal flap 105 having a base end 106 on a proximal side and a free end 107 on a distal side on the proximal side of the tubular member 104, and a distal flap 108 having a base end 109 on the distal side and a free end 110 on the proximal side on the distal side of the tubular member 104. The in-vivo indwelling tube 1 has a proximal end 102 and a distal end 103 and extends axially. The base end 106 is a base point at which the proximal flap 105 rises from the tubular member 104, and the free end 107 is a tip of the proximal flap 105 raised from the tubular member 104. The base end 109 is a base point at which the distal flap 108 rises from the tubular member 104, and the free end 110 is a tip of the distal flap 108 raised from the tubular member 104.

As shown in FIGS. 2 to 5, the tubular member 104 includes, radially outward of the tubular member 104, at least either the distal side first supporting member 10 provided on the distal side of a midpoint P3 between the base end 109 and the free end 110 of the distal flap 108 or a proximal side first supporting member 30 provided on the proximal side of a midpoint P4 between the base end 106 and the free end 107 of the proximal flap 105. FIGS. 2 to 5 show an example in which the tubular member 104 is provided with both the distal side first supporting member 10 and the proximal side first supporting member 30. That is, the proximal end 10a of the distal side first supporting member 10 is disposed on the distal side of the midpoint P3 between the base end 109 and the free end 110 of the distal flap 108, and the distal end 30b of the proximal side first supporting member 30 is disposed on the proximal side of the midpoint P4 between the base end 106 and the free end 107 of the proximal flap 105. The distal side first supporting member 10 is disposed in the vicinity of the distal flap 108 of the tubular member 104 to prevent the base end 109 from being torn by the stress applied on the base end 109 of the distal flap 108 and breaking the distal flap 108. Similar to the distal side first supporting member 10, the proximal side first supporting member 30 is also disposed in the vicinity of the proximal flap 105 of the tubular member 104 to prevent the base end 106 from being torn by the stress applied on the base end 106 of the proximal flap 105 and breaking the proximal flap 105. Further details of the distal side first supporting member 10 and the proximal side first supporting member 30 will be described later.

(3) Tubular Member

The inner diameter of the tubular member 104 may be constant over the entire axial direction or may differ depending on the axial position.

The outer diameter of the distal end 103 of the tubular member 104 is preferably smaller than the average outer diameter of the tubular member 104 between the position of the tubular member 104 corresponding to the free end 110 of the distal flap 108 and the position of the tubular member 104 corresponding to the free end 107 of the proximal flap 105. The outer diameter of the tubular member 104 may be reduced in a tapered manner towards the distal end 103 at the distal end portion. Since the outer diameter of the distal end 103 of the tubular member 104 is reduced, the in-vivo indwelling tube 1 can easily pass through the constricted portion or the occluded portion of the lumen in the living body.

The thickness of the tubular member 104 can be appropriately set according to the required strength and flexibility, but is preferably 0.2 mm or more and 0.6 mm or less. The strength of the in-vivo indwelling tube 1 can be made sufficient, and flexibility can be given to the in-vivo indwelling tube 1 by setting the thickness of the tubular member 104 in this manner.

The thickness of the proximal end 102 of the tubular member 104 is preferably thicker than the average thickness of the tubular member 104 between the position of the tubular member 104 corresponding to the free end 110 of the distal flap 108 and the position of the tubular member 104 corresponding to the free end 107 of the proximal flap 105. With this thickness of the proximal end 102 of the tubular member 104, the pushability of the in-vivo indwelling tube 1 can be improved. The end face of the proximal end 102 is preferably flat. Thus, the strength of the end face of the proximal end 102 of the in-vivo indwelling tube 1 becomes constant, and the pushability of the in-vivo indwelling tube 1 can be improved. Furthermore, the end face of the proximal end 102 may be chamfered at its outer periphery so as not to damage the body cavity.

Examples of a material that constitutes the tubular member 104, the proximal flap 105, and the distal flap 108 include polyamide resins, polyester resins, polyurethane resins, polyolefin resins, fluorine resins, vinyl chloride resins, silicone resins, natural rubbers, and the like. Only one kind of resin may be used or two or more kinds of resins may be simultaneously used. Among them, polyamide resins, polyester resins, polyurethane resins, polyolefin resins and fluorine resins are suitably used. The material that constitutes the tubular member 104, the proximal flap 105, and the distal flap 108 may be the same or may be different. If the material that constitutes the tubular member 104, the proximal flap 105, and the distal flap 108 is the same, the overall strength and flexibility of the in-vivo indwelling tube 1 become uniform. Furthermore, the in-vivo indwelling tube 1 in which the holding force of the proximal flap 105 and the distal flap 108 to the lumen in the living body is high but the flexibility of the tubular member 104 is maintained is obtained by having the material configuring the proximal flap 105 and the distal flap 108 as a material having a higher hardness than the material configuring the tubular member 104.

(4) First Region and Second Region

As shown in FIG. 2, the tubular member 104 includes a first region 50 and a second region 60 sequentially from the proximal side, and preferably has the colors of the first region 50 and the second region 60 different from each other on the distal side of the base end 106 of the proximal flap 105. The colors of the first region 50 and the second region 60 being different from each other indicates that at least one of the hue, the lightness, and the saturation defined in JIS Z8721 is different between the color of the first region 50 and the color of the second region 60. Since the tubular member 104 includes the first region 50 and the second region 60, and the colors of the first region 50 and the second region 60 are different from each other, the position of the proximal flap 105 of the in-vivo indwelling tube 1 can be easily confirmed with an endoscope when transporting the in-vivo indwelling tube 1 to a desired location in the lumen in the living body. If the color of the second region 60 is a color different from that of the first region 50 and is a color that is easily visible under an endoscope, the boundary between the first region 50 and the second region 60 can be easily confirmed and the proximal flap 105 of the in-vivo indwelling tube 1 can be easily confirmed. For example, the color of the first region 50 may be a color with low lightness such as black, and the color of the second region 60 may be a color with high lightness such as yellow. Furthermore, the color of the first region 50 may be a color with high lightness, and the color of the second region 60 may be a color with low lightness.

Apart from the first region 50 and the second region 60, the tubular member 104 may include a region having a color different from at least either the first region 50 or the second region 60 on the proximal side of the base end 106 of the proximal flap 105. If the tubular member 104 includes a region different in color on the proximal side of the base end 106 of the proximal flap 105, the proximal end 102 and the distal end 103 of the in-vivo indwelling tube 1 can be easily distinguished. In addition, if the region having a different color is not provided on the proximal side of the base end 106 of the proximal flap 105, the first region 50 becomes noticeable, and the visibility of the first region 50 in the endoscope enhances.

A method for making the colors of the first region 50 and the second region 60 different from each other includes, for example, a method of coloring at least one of the portion to become the first region 50 and the portion to become the second region 60 in the tubular member 104, a method of disposing a film or a tubular member different in color from the tubular member 104 in at least one of the portion to become the first region 50 and the portion to become the second region 60, and the like. A method of coloring at least one of the portion to become the first region 50 and the portion to become the second region 60 of the tubular member 104 includes a method of applying paint, a method of dyeing with dye, and the like. Among them, it is preferable to apply and color a paint having a color different from that of the tubular member 104 to the portion to become the first region 50 of the tubular member 104. The visibility of the position of the proximal flap 105 of the in-vivo indwelling tube 1 in the endoscope can be enhanced by making the colors of the first region 50 and the second region 60 different from each other as described above. Furthermore, the tubular member 104 may include a region of a color different from the second region 60 on the distal side of the second region 60. The color of the proximal side second supporting member 40 to be described later may be different from the color of the first region 50, and the proximal side second supporting member 40 may be assumed as the second region 60.

The axial length of the first region 50 and the second region 60 can be appropriately set so as to be easily visible. The proximal end 50*a* of the first region 50 is preferably on the proximal side of the base end 106 of the proximal flap 105 of the tubular member 104, and the distal end 50*b* of the first region 50 is preferably on the distal side of the base end 106 of the proximal flap 105 of the tubular member 104. The proximal end 50*a* of the first region 50 may be on the distal side of the base end 106 of the proximal flap 105 of the tubular member 104. Furthermore, the proximal end 50a of the first region 50 may coincide with the proximal end 102 of the tubular member 104.

As shown in FIGS. 7 to 9, the proximal end 60a of the second region 60 is preferably disposed on the distal side than the position P2 of the tubular member 104 corresponding to the free end 107 of the proximal flap 105. The position P2 of the tubular member 104 corresponding to the free end 107 of the proximal flap 105 is the position where the free end 107 of the proximal flap 105 comes into contact with the tubular member 104 when the proximal flap 105 is arranged along the tubular member 104 and the proximal flap 105 is closed.

(5) Proximal Flap and Distal Flap

The proximal flap 105 is provided at the proximal portion of the tubular member 104 and the distal flap 108 is provided at the distal portion of the tubular member 104. The proximal flap 105 and the distal flap 108 may be formed, for example, by forming a cut on the surface of the end portion of the tubular member 104. Alternatively, it may be formed by providing a flap member, which forms the proximal flap 105 or the distal flap 108 and is a member different from the tubular member 104, at the proximal end or the distal end of the tubular member 104. In this case, a method for joining the flap member to the tubular member 104, and the like can be adopted. The proximal flap 105 and the distal flap 108 may be formed through the same method or may be formed through different methods.

When joining the proximal flap member or the distal flap member to the outer surface of the tubular member 104 to form a flap, the flap member may be formed of a material same as or different from the material that constitutes the tubular member 104. A method of joining the tubular member 104 and the flap member includes thermal welding, ultrasonic welding, adhesion by an adhesive, and the like, but joining by thermal welding is preferable. The joining strength of the tubular member 104 and the flap member can be enhanced by joining the tubular member 104 and the flap member by thermal welding.

When there is a lesion such as a cancer near the papilla of the duodenum, there is a possibility that the vicinity of the proximal flap 105 of the in-vivo indwelling tube 1 may come in contact with the lesion. In this case, if there is a hole formed by cutting the tubular member 104 to form the proximal flap 105 in the vicinity of the proximal flap 105 of the tubular member 104, the cancer cells and the like may enter the lumen of the in-vivo indwelling tube 1 from the hole thus blocking or constricting the lumen of the in-vivo indwelling tube 1. Therefore, when there is a possibility that a lesion such as a cancer may come in contact with the vicinity of the proximal flap 105, and the like, the proximal flap 105 is preferably formed by providing the proximal flap member in the tubular member 104 so as not to form a hole having a size of an extent the cancer cells and the like can enter to the vicinity of the proximal flap 105.

The strength of the distal flap 108 is preferably increased to prevent breakage of the distal flap 108 when collecting the in-vivo indwelling tube 1 from the living body. In order to increase the strength of the distal flap 108, the distal flap 108 and the tubular member 104 are preferably formed integrally by forming a cut at the distal end portion of the tubular member 104.

The proximal flap 105 extends axially and radially outward from the proximal side to the distal side. The distal flap 108 extends axially and radially outward from the distal side to the proximal side. One or more of the proximal flap 105 and the distal flap 108 may be provided, for example, two or more, three or more, or five or less. When a plurality of proximal flaps 105 or distal flaps 108 are provided, the flaps are preferably arranged at equal intervals in the circumferential direction of the tubular member 104. With the plurality of proximal flaps 105 arranged in this manner, the effect of preventing the proximal end 102 of the in-vivo indwelling tube 1 from entering the lumen in the living body can be enhanced. With the plurality of distal flaps 108 arranged in this manner, the effect of preventing the in-vivo indwelling tube 1 from falling out of the lumen in the living body can be enhanced. Furthermore, when a plurality of proximal flaps 105 or distal flaps 108 are provided, the length from the base end to the free end of the flap to be described later, and the width and thickness of the flaps may be all the same or may be different. For example, if the length, width, and thickness of each flap are the same, production becomes easy. Furthermore, the strength of each flap can be changed by changing the length, width, and thickness of each flap. Specific examples include increasing the strength of the flap in an area where stress is likely to be applied and there is a possibility of breakage, and decreasing the strength of the flap in an area where flexibility is required.

The length from the base end 106 to the free end 107 of the proximal flap 105 and the length from the base end 109 to the free end 110 of the distal flap 108 are not particularly limited, but are preferably 4 mm or more and 15 mm or less. The flap can have sufficient elasticity, and the in-vivo indwelling tube 1 can be prevented from entering to other than the desired position by setting the length from the base end to the free end of the flap in this manner.

The thickness of the proximal flap 105 is not particularly limited, but the lumen in the living body that comes into contact with the proximal flap 105 can be made to be less likely to be damaged by making the thickness of the proximal flap 105 thinner than the thickness of the proximal end of the tubular member 104. The strength of the proximal flap 105 can be increased by making the thickness of the proximal flap 105 thicker than the thickness of the proximal end of the tubular member 104. Furthermore, the thickness of the proximal flap 105 may be constant or may be different from the base end 106 to the free end 107. For example, the proximal flap may include a portion where the thickness decreases from the base end 106 toward the free end 107 of the proximal flap 105.

The thickness of the distal flap 108 is not particularly limited, but is preferably thinner than the thickness of the proximal end 102 of the tubular member 104. The distal flap 108 can be prevented from penetrating or damaging the wall of the lumen in the living body by making the thickness of the distal flap 108 thinner than the thickness of the proximal end 102 of the tubular member 104. Furthermore, the thickness of the distal flap 108 is preferably thicker than the average thickness of the tubular member 104 between the position of the tubular member 104 corresponding to the free end 110 of the distal flap 108 and the position of the tubular member 104 corresponding to the free end 107 of the proximal flap 105. This thickness of the distal flap 108 can enhance the retention of the distal flap 108 in the lumen in the living body.

The thickness and length of the proximal flap 105 and the distal flap 108 may be the same or may be different. For example, by making the length of the proximal flap 105 longer than the length of the distal flap 108, the proximal flap 105 can be greatly opened radially outward, and the effect of preventing the proximal end 102 of the in-vivo indwelling tube 1 from entering the lumen in the living body can be enhanced. By making the length of the distal flap 108 longer than the length of the proximal flap 105, the opening size of the distal flap 108 can be increased, and the holding force to the lumen in the living body can be increased. If the thickness of the proximal flap 105 is thinner than the thickness of the distal flap 108, the proximal flap 105 is less likely to interfere with the inner wall of the conduit of the endoscope, which has an effect of improving the delivery performance. If the thickness of the proximal flap 105 is thicker than the thickness of the distal flap 108, the strength of the proximal flap 105 is increased and the effect of preventing the proximal end 102 of the in-vivo indwelling tube 1 from entering the lumen in the living body can be enhanced. The thickness of the proximal flap 105 and the distal flap 108 is preferably 0.2 mm or more and 0.6 mm or less. The thickness of the flap may be constant or may be different from the base end to the free end of the flap.

The material that constitutes the proximal flap 105 and the distal flap 108 is not particularly limited, and those listed as the resin that constitutes the tubular member 104 can be used. The material that constitutes the flap may be the same as or different from the material that constitutes the tubular member 104. If the material that constitutes the flap and the material that constitutes the tubular member 104 are the same, the joinability between the tubular member 104 and the flap is improved, and the flap is easily provided on the tubular member 104. If the material that constitutes the flap and the material that constitutes the tubular member 104 are different, for example, a soft material is used for the material that constitutes the tubular member 104 so that the in-vivo indwelling tube 1 in which the flexibility of the tubular member 104 is high but the strength of the flap is high is obtained.

The type A durometer hardness of the material that constitutes the proximal flap 105 is preferably higher than the average type A durometer hardness of the material that constitutes the tubular member 104 between the position of the tubular member 104 corresponding to the free end 110 of the distal flap 108 and the position of the tubular member 104 corresponding to the free end 107 of the proximal flap 105. Type A durometer hardness can be measured by a method conforming to JIS K7215. The rigidity of the proximal flap 105 can be increased and the function of fixing the in-vivo indwelling tube 1 in the lumen in the living body can be enhanced by increasing the hardness of the material that constitutes the proximal flap 105.

(6) Preferred Arrangement of Distal Side First Supporting Member and Proximal Side First Supporting Member As shown in FIG. 3, preferably, the distal side first supporting member 10 is provided on the proximal side of the base end 109 of the distal flap 108, and the proximal side first supporting member 30 is provided on the distal side of the base end 106 of the proximal flap 105. That is, preferably, the proximal end 10a of the distal side first supporting member 10 is arranged on the distal side of the midpoint P3 of the base end 109 and the free end 110 of the distal flap 108, and the distal end 10b of the distal side first supporting member 10 is arranged on the proximal side of the base end 109 of the distal flap 108. Furthermore, preferably, the distal end 30b of the proximal side first supporting member 30 is arranged on the proximal side of the midpoint P4 of the base end 106 and the free end 107 of the proximal flap 105, and the proximal end 30a of the proximal side first supporting member is arranged on the distal side of the base end 106 of the proximal flap 105. When stress is applied to the distal flap 108, the stress can be received by the distal side first supporting member 10 by arranging the distal side first supporting member 10 in such a manner. As a result, stress can be prevented from being applied to the base end 109 of the distal flap 108 thus tearing the base end 109, and the tear of the base end 109 can be prevented from reaching the distal end 103 of the tubular member 104 and breaking the distal flap 108. Furthermore, similar to the distal side first supporting member 10, when stress is applied to the proximal flap 105, the stress can be received by the proximal side first supporting member 30 by arranging the proximal side first supporting member 30 in such a manner, and the proximal flap 105 can be prevented from breaking.

As shown in FIG. 4, preferably, the distal side first supporting member 10 is provided on the base end 106 of the distal flap 108, and the proximal side first supporting member 30 is provided on the base end 106 of the proximal flap 105. That is, preferably, the proximal end 10a of the distal side first supporting member 10 is arranged on the distal side of the midpoint P3 of the base end 109 and the free end 110 of the distal flap 108 and on the proximal side of the base 109, and the distal end 10b of the distal side first supporting member 10 is arranged on the distal side of the base end 109. Furthermore, preferably, the distal end 30b of the proximal side first supporting member 30 is arranged on the proximal side of the midpoint P4 of the base end 106 and the free end 107 of the proximal flap 105 and on the distal side of the base end 106, and the proximal end 30a of the proximal side first supporting member is arranged on the proximal side of the base end 106. The stress applied to the distal flap 108 can be received by the distal side first supporting member 10 by arranging the distal side first supporting member 10 in such a manner. Therefore, stress can be prevented from being applied to the base end 109 of the distal flap 108 thus tearing the base end 109 and breaking the distal flap 108. Furthermore, similar to the distal side first supporting member 10, when stress is applied to the proximal flap 105, the stress applied to the proximal flap 105 can be received by the proximal side first supporting member 30 by arranging the proximal side first supporting member 30 in such a manner, and the proximal flap 105 can be prevented from breaking.

As shown in FIG. 5, preferably, the distal side first supporting member 10 is provided on the proximal side of a midpoint P5 between the base end 109 of the distal flap 108 and the distal end 103 of the tubular member 104, and the proximal side first supporting member 30 is provided on the distal side of a midpoint P6 between the base end 106 of the proximal flap 105 and the proximal end 102 of the tubular member 104. That is, preferably, the proximal end 10a of the distal side first supporting member 10 is arranged on the distal side of the midpoint P3 of the base end 109 and the free end 110 of the distal flap 108 and on the distal side of the base end 109, and the distal end 10b of the distal side first supporting member 10 is arranged on the proximal side of the midpoint P5 between the base end 109 and the distal end 103 of the tubular member 104. Furthermore, preferably, the distal end 30b of the proximal side first supporting member 30 is arranged on the proximal side of the midpoint P4 of the base end 106 and the free end 107 of the proximal flap 105 and on the proximal side of the base end 106, and the proximal end 30a of the proximal side first supporting member 30 is arranged on the distal side of the midpoint P6 between the base end 106 and the proximal end 102 of the tubular member 104. By arranging the distal side first supporting member 10 in this manner, even if stress is applied to the base end 109 of the distal flap 108 and the base end 109 is partially torn, the base end 109 can be prevented from being torn to the distal end 103 of the tubular member 104 beyond the distal side first supporting member 10, and breakage of the distal flap 108 can be prevented. Furthermore, similar to the distal side first supporting member 10, when stress is applied to the proximal flap 105, the stress can be received by the proximal side first supporting member 30 by arranging the proximal side first supporting member 30 in such a manner, and the proximal flap 105 can be prevented from breaking.

(7) Distal Side Second Supporting Member and Proximal Side Second Supporting Member At least either the distal side second supporting member 20 or the proximal side second supporting member 40 may be provided to increase the strength of the entire in-vivo indwelling tube 1. Specifically, at least either the distal side second supporting member 20 provided on the proximal side of the free end 110 of the distal flap 108 and on the distal side of a midpoint P9 of the tubular member 104 and the proximal side second supporting member 40 provided on the distal side of the free end 107 of the proximal flap 105 and on the proximal side of the midpoint P9 of the tubular member 104 may be provided. For example, it may become difficult to transport the in-vivo indwelling tube 1 to the desired indwelling portion as the portion of low strength of the tubular member 104 in the vicinity of the distal flap 108 is excessively bent. Thus, the strength of the entire in-vivo indwelling tube 1 can be increased and the pushability can be enhanced by providing the distal side second supporting member 20 or the proximal side second supporting member 40 at the portion where the strength of the in-vivo indwelling tube 1 is to be increased.

(8) Configuration of Distal Side First Supporting Member, Distal Side Second Supporting Member, Proximal Side First Supporting Member and Proximal Side Second Supporting Member The in-vivo indwelling tube 1 is provided with at least either the distal side first supporting member or the proximal side first supporting member. In addition to the distal side first supporting member and the proximal side first supporting member, the in-vivo indwelling tube 1 is provided with at least either the distal side second supporting member or the proximal side second supporting member.

The shape of each supporting member is not particularly limited, but is preferably tubular, and includes a cylindrical shape, a polygonal tubular shape, a shape having C-shaped cross section in which a slit is formed in a tube, and a coil shape in which a wire is wound. Among them, the shape of at least one of the distal side first supporting member 10, the distal side second supporting member 20, the proximal side first supporting member 30, and the proximal side second supporting member 40 is preferably a tubular shape. Since the shape of the distal side first supporting member 10 is tubular, when an external force is applied to the distal flap 108, the external force can be received by the entire distal side first supporting member 10 and the distal flap 108 can be prevented from breaking. Since the shape of the proximal side first supporting member 30 is tubular, when an external force is applied to the proximal flap 105, the external force can be received by the entire proximal side first supporting member 30 and the proximal flap 105 can be prevented from breaking. When the shape of at least either the distal side second supporting member 20 or the proximal side second supporting member 40 is tubular, an effect of increasing the strength in an area where at least either the distal side second supporting member 20 or the proximal side second supporting member 40 of the in-vivo indwelling tube 1 is provided is obtained. The shapes of all the supporting bodies provided in the in-vivo indwelling tube may be the same or may be different.

The axial length of the first supporting member, which is the length from the proximal end to the distal end of the first supporting member, is not particularly limited, where the effect of preventing the flap from breaking is enhanced by increasing the length of the supporting member and the flexibility of the in-vivo indwelling tube 1 can be maintained by decreasing the length. The axial length of the first supporting member can be appropriately selected according to the required effect. Similarly to the axial length of the first supporting member, the axial length of the second supporting member can be set according to the necessary effect. The length of each supporting member may be the same or may be different. In FIG. 3, the axial length of the distal side first supporting member 10 is the length from the proximal end 10a to the distal end 10b of the distal side first supporting member. Similarly, the axial length of the proximal side first supporting member 30 is the length from the proximal end 30a to the distal end 30b of the proximal side first supporting member 30.

The thickness of the supporting member is not particularly limited, but the effect of preventing the flap from breaking is enhanced by increasing the thickness of the supporting member. When the thickness of the supporting member is reduced, the flexibility of the in-vivo indwelling tube 1 is enhanced, and the step difference between the supporting member and the tubular member is reduced. As a result, the in-vivo indwelling tube 1 can be easily transported to the lesion.

The inner diameter of at least one of the supporting bodies is preferably smaller than the outer diameter of the tubular member 104. Thus, the supporting member is firmly fixed to the tubular member 104, and the supporting member is less likely to be detached from the in-vivo indwelling tube 1. In order to make the inner diameter of the supporting member smaller than the outer diameter of the tubular member 104, for example, a method of forming the supporting member with metal, forming a cut in the axial direction of the supporting member and placing the supporting member radially outward of the tubular member 104 and then caulking the supporting member to overlap the portion with the cut of the supporting member to reduce the inner diameter of the supporting member, or forming the supporting member with a heat-shrinkable resin to a tubular shape in which the inner diameter of the supporting member is larger or equal to the outer diameter of the tubular member 104 and applying heat to the supporting member to shrink the inner diameter of the supporting member more than the outer diameter of the tubular member 104.

The material that constitutes the supporting member is not particularly limited, and for example, includes metals, such as stainless steel, titanium, cobalt chromium alloy, and platinum iridium alloy, resins such as polyamide resin, polyester resin, polyurethane resin, polyolefin resin, fluorine resin, vinyl chloride resin, silicone resin, natural rubber, and the like. Among them, the material that constitutes at least one of the supporting bodies is preferably higher in strength than the material that constitutes the tubular member 104.

A material having a higher strength than that of the material that constitutes the tubular member 104 includes, for example, metal and resin having a higher type A durometer hardness higher than that of the material that constitutes the tubular member 104. That is, when the material that constitutes at least one of the supporting bodies is a resin, the type A durometer hardness of the material is preferably higher than the type A durometer hardness of the material that constitutes the tubular member 104. Type A durometer hardness can be measured by a method conforming to JIS K7215. As the material that constitutes the first supporting member has a higher strength than the material that constitutes the tubular member 104, the base of the flap can be prevented from being torn to the end portion of the tubular member 104 and the breakage of the flap can be prevented.

Since the position of the in-vivo indwelling tube 1 can be detected by X-ray fluoroscopy or the like, the material that constitutes at least one of the supporting bodies may include a radiopaque material. In order to increase the visibility of the in-vivo indwelling tube 1 under an endoscope, the material that constitutes at least one of the supporting bodies is preferably a color different from that of the tubular member 104 or a material different from that of the tubular member 104. For example, the proximal side second supporting member 40 may be the second region 60 by making the color of the proximal side second supporting member 40 different from the color of the first region 50 of the tubular member 104.

One or more supporting bodies may be provided on the tubular member 104, for example, two or more or four or less. For example, in the case where the distal side first supporting member 10 is provided in plurals on the tubular member 104, the effect of preventing the breakage of the distal flap 108 can be further enhanced.

As shown in FIG. 6, preferably, the midpoint P7 between the proximal end 10a of the distal side first supporting member 10 and the distal end 20b of the distal side second supporting member 20 is on the distal side of the free end 110 of the distal flap 108, and the midpoint P8 between the distal end 30b of the proximal side first supporting member 30 and the proximal end 40a of the proximal side second supporting member 40 is on the proximal side of the free end 107 of the proximal flap 105. For example, when the distal flap 108 is formed by forming a cut on the distal side of the tubular member 104, the strength in the vicinity of the distal flap 108 of the in-vivo indwelling tube 1 decreases, so that the vicinity of the distal flap 108 of the in-vivo indwelling tube 1 may be bent, and the pushability of the in-vivo indwelling tube 1 may be reduced in transporting the in-vivo indwelling tube 1 to the desired indwelling portion of the lumen in the living body. The same applies to the proximal flap 105, and when the proximal flap is formed by forming a cut on the proximal side of the tubular member 104, the vicinity of the proximal flap 105 of the in-vivo indwelling tube 1 may be bent and the pushability of the in-vivo indwelling tube 1 may be reduced. Therefore, the strength in the vicinity of the distal flap 108 of the in-vivo indwelling tube 1 can be enhanced by the distal side first supporting member 10 and the distal side second supporting member 20, the strength in the vicinity of the proximal flap 105 of the in-vivo indwelling tube 1 can be enhanced by the proximal side first supporting member 30 and the proximal side second supporting member 40 and the bend of the distal flap 108 and the proximal flap 105 can be prevented by arranging the distal flap 108, the distal side first supporting member 10, and the distal side second supporting member 20 in such a manner and arranging the proximal flap 105, the proximal side first supporting member 30, and the proximal side second supporting member 40 in such a manner.

(9) Configuration Including Larger Diameter Portion

As shown in FIG. 7, the in-vivo indwelling tube 1 preferably includes a larger diameter portion 111 in which the maximum outer diameter is larger than the average outer diameter of the tubular member 104 between the position P1 of the tubular member 104 corresponding to the free end 110 of the distal flap 108 or the proximal end 20a of the distal side second supporting member 20 and the position P2 of the tubular member 104 corresponding to the free end 107 of the proximal flap 105 or the distal end 50b of the first region 50 on at least one of the proximal side of the base end 106 of the proximal flap 105 and the distal side of the base end 109 of the distal flap 108. The position P1 of the tubular member 104 corresponding to the free end 110 of the distal flap 108 is the position where the free end 110 of the distal flap 108 comes into contact with the tubular member 104 when the distal flap 108 is arranged along the tubular member 104 and the distal flap 108 is closed. The position P2 of the tubular member 104 corresponding to the free end 107 of the proximal flap 105 is the position where the free end 107 of the proximal flap 105 comes into contact with the tubular member 104 when the proximal flap 105 is arranged along the tubular member 104 and the proximal flap 105 is closed. The strength of the proximal flap 105 can be enhanced and the breakage of the proximal flap 105 can be prevented by including the larger diameter portion 111 on the proximal side of the base end 106 of the proximal flap 105. Similarly, the strength of the distal flap 108 can be enhanced by including the larger diameter portion 111 on the distal side of the base end 109 of the distal flap 108.

In order to form the larger diameter portion 111 on the proximal side of the base end 106 of the proximal flap 105, for example, a flap member configuring the proximal flap 105 may be disposed in an overlapping manner radially outward of the tubular member 104 and the flap member may be joined to the outer surface of the tubular member 104. Since the outer diameter is large at the portion where the flap member and the tubular member 104 are joined to each other, the larger diameter portion 111 is formed on the proximal side of the base end 106 of the proximal flap 105 of the in-vivo indwelling tube 1. Furthermore, a hole does not form in the vicinity of the base end 106 of the proximal flap 105, and a lesion such as a cancer cell can be prevented from entering the lumen of the in-vivo indwelling tube 1 through the hole by producing the in-vivo indwelling tube 1 in such a manner.

In order to form the larger diameter portion 111 on the distal side of the base end 109 of the distal flap 108, similar to the method of forming the larger diameter portion 111 on the proximal side of the base end 106 of the proximal flap 105, a method of arranging a flap member configuring the distal flap 108 in an overlapping manner radially outward of the tubular member 104 and joining the flap member to the outer surface of the tubular member 104, and the like may be adopted. Since the outer diameter becomes large at the portion where the flap member and the tubular member 104 are joined to each other by forming the distal flap 108 in such a manner, the larger diameter portion 111 is formed on the distal side of the base end 109 of the distal flap 108 of the in-vivo indwelling tube 1.

(10) Configuration Including Smaller Diameter Portion

Preferably, the smaller diameter portion is provided between the base of the flap and the free end of the flap in the closed state. The axial length of the smaller diameter portion is preferably smaller than the length from the base of the flap to the free end of the flap in the closed state. As shown in FIG. 8, the tubular member 104 preferably includes a smaller diameter portion 114 in which the minimum outer diameter is smaller than the average outer diameter of the tubular member 104 between the position P1 of the tubular member 104 corresponding to the free end 110 of the distal flap 108 or the proximal end 20a of the distal side second supporting member 20 and the position P2 of the tubular member 104 corresponding to the free end 107 of the proximal flap 105 or the distal end 50b of the first region 50, where the smaller diameter portion 114 is preferably provided on at least either between the base end 106 of the proximal flap 105 and the position on the proximal side of the free end 107 of the proximal flap 105 when the proximal flap 105 is in the closed state or between the base end 109 of the distal flap 108 and the position on the distal side of the free end 110 of the distal flap 108 when the distal flap 108 is in the closed state. In this case, as shown in FIG. 9, preferably, at least either the free end 107 of the proximal flap 105 when the proximal flap 105 is in the closed state being on the distal side of the distal end 116 of the smaller diameter portion 114, or the free end 110 of the distal flap 108 when the distal flap 108 is in the closed state being on the proximal side of the proximal end 115 of the smaller diameter portion 114 is obtained. The closed state of the flap is a state in which the flap is closed along the tubular member 104. The smaller diameter portion 114 may have a hole to be described later so that the minimum outer diameter may be smaller than the average outer diameter of the tubular member 104 between the position P1 of the tubular member 104 corresponding to the free end 110 of the distal flap 108 or the proximal end 20a of the distal side second supporting member 20 and the position P2 of the tubular member 104 corresponding to the free end 107 of the proximal flap 105 or the distal end 50b of the first region 50. Furthermore, the smaller diameter portion 114 may have the minimum outer diameter made smaller than the average outer diameter of the tubular member 104 by reducing the entire outer diameter of the tubular member 104 between the position P1 of the tubular member 104 corresponding to the free end 110 of the distal flap 108 or the proximal end 20a of the distal side second supporting member 20 and the position P2 of the tubular member 104 corresponding to the free end 107 of the proximal flap 105 or the distal end 50b of the first region 50.

With the smaller diameter portion 114 provided between the base end 106 of the proximal flap 105 and the position on the proximal side of the free end 107 of the proximal flap 105 when the proximal flap 105 is in the closed state, the outer diameter of the tubular member 104 in an area where the tubular member 104 and the proximal flap 105 overlap when the proximal flap 105 is in the closed state can be reduced. With the smaller diameter portion 114 provided between the base end 109 of the distal flap 108 and the position on the distal side of the free end 110 of the distal flap 108 when the distal flap 108 is in the closed state, the outer diameter of the tubular member 104 in an area where the tubular member 104 and the distal flap 108 overlap when the distal flap 108 is in the closed state can be reduced. The inner wall of the conduit is less likely to interference with the in-vivo indwelling tube 1 and smooth passing of the conduit is realized when passing the in-vivo indwelling tube 1 through the conduit of the endoscope and the like by reducing the outer diameter of the tubular member 104 in an area where the tubular member 104 and the flap overlap.

In order to form the smaller diameter portion 114 between the base end 106 of the proximal flap 105 and the position on the proximal side of the free end 107 of the proximal flap 105 when the proximal flap 105 is in the closed state or between the base end 109 of the distal flap 108 and the position on the distal side of the free end 110 of the distal flap 108 when the distal flap 108 is in the closed state, for example, a method of scraping off the proximal end portion of the tubular member 104 and forming an opening in the tubular member 104 and placing a flap member configuring the flap in the opening, a method of forming the proximal end portion of the tubular member 104 with three types of components of flap containing tube component that configures the flap, a distal side tube component arranged on the distal side of the flap containing tube component, and a lumen tube component placed in the lumen of the flap containing tube component and the distal side tube component and placing the proximal end of the distal side tube component on the distal side or the proximal side of the base of the flap of the flap containing tube component, and the like, are adopted. Thus, the smaller diameter portion 114 is formed on the distal side or the proximal side of the base of the flap of the in-vivo indwelling tube 1, and the outer diameter of an area where the tubular member 104 and the flap overlap can be reduced in a state where the flap is closed along the tubular member 104 by producing the in-vivo indwelling tube 1 in such a manner.

As shown in FIGS. 10 and 11, the conventional in-vivo indwelling tube 201 is formed with a cut in the tubular member 204 to form the proximal flap 205. Therefore, in a state in which the proximal flap 205 is arranged along the tubular member 204 and the proximal flap 205 is closed, the free end 207 of the proximal flap 205 is located on the proximal side of the distal end 216 of the smaller diameter portion 214. Similarly for the distal flap 208, the tubular member 204 is formed with a cut to form the distal flap 208. Therefore, in a state in which the distal flap 208 is arranged along the tubular member 204 and the distal flap 208 is closed, the free end 210 of the distal flap 208 is located on the distal side of the proximal end 215 of the smaller diameter portion 214.

As shown in FIGS. 8 and 9, in the in-vivo indwelling tube 1 of the present invention, when the smaller diameter portion 114 is provided between the base end 106 of the proximal flap 105 and the position on the proximal side of the free end 107 of the proximal flap 105 when the proximal flap 105 is in the closed state, the free end 107 of the proximal flap 105 is located on the distal side of the distal end 116 of the smaller diameter portion 114 in a state the proximal flap 105 is closed. Furthermore, the axial length of the smaller diameter portion 114 is preferably shorter than the axial length of the proximal flap 105.

When the smaller diameter portion 114 is provided between the base end 109 of the distal flap 108 and the position on the distal side of the free end 110 of the distal flap 108 when the distal flap 108 is in a closed state, the free end 110 of the distal flap 108 is located on the proximal side of the proximal end 115 of the smaller diameter portion 114 in a state the distal flap 108 is closed. The axial length of the smaller diameter portion 114 is preferably shorter than the axial length of the distal flap 108.

For the position of the smaller diameter portion 114, the smaller diameter portion 114 is preferably provided between the base end of the flap and the position of the free end of the flap when the flap is in the closed state. The smaller diameter portion may be provided biased toward the base end side or the free end side of the flap. In particular, it is preferably provided on the base end side of the flap.

The tubular member 104 may have a hole at the smaller diameter portion 114. The hole may be a through hole that communicates the lumen of the tubular member 104 and the exterior of the tubular member 104. Alternatively, the hole may be a recess on the tubular member 104 that does not communicate the lumen of the tubular member 104 and the exterior of the tubular member 104.

The cross-sectional area of the hole in the plane perpendicular to the depth direction of the hole is not particularly limited, but is preferably smaller than the maximum cross-sectional area of the lumen of the tubular member 104. If the hole has such a size, even if a lesion such as a cancer cell comes into contact with the hole, the lesion can be made less likely to enter the lumen of the in-vivo indwelling tube 1.

The shape of the hole is not particularly limited, and examples thereof include a circle, an ellipse, a rectangle and a polygon. Moreover, the length of the hole in the axial direction of the tubular member 104 may be over the entire region of the smaller diameter portion 114 or may be shorter than the length from the distal end 116 to the proximal end 115 of the smaller diameter portion 114.

The position of the hole may extend from the base end of the flap to the position of the free end when the flap is in the closed state, or may be smaller. The length of the hole in the direction orthogonal to the axial direction of the tubular member 104 is preferably shorter than the length in the direction orthogonal to the axial direction of the proximal flap 105. Such a shape of the hole allows the possibility of a lesion such as a cancer cell entering the lumen of the in-vivo indwelling tube 1 through the hole to be reduced.

An example of the production method of the in-vivo indwelling tube 1 including the supporting member will be described below. In the case of the present production method, the tubular member 104 has a multilayered structure including an inner tube and an outer tube, and a supporting member is disposed between the layers of the tubular member 104. According to the present production method, the flap or the supporting member can be disposed at the desired position.

First, the inner tube is covered with a supporting member. The supporting member may have a ring shape, a plate shape, or a C shape. When the supporting member has a ring shape, the supporting member is passed through the inner tube to place the supporting member on the inner tube. Furthermore, when the supporting member has a plate shape, the supporting member is rounded to a shape along the outer periphery of the inner tube, and the end portion is fixed to place the supporting member on the inner tube. After the ring shaped or C shaped supporting member is placed on the inner tube, the diameter of the supporting member may be reduced to be attached in an inner tube form. The fixing of the end portion of the plate shaped or C shaped supporting member can be performed using an arbitrary method such as welding or adhesion.

Next, the outer tube is placed over at least a part of the supporting member of the inner tube. The outer tube merely needs to have a length that covers at least the supporting member, and may be the same length as the inner tube or longer than the inner tube. The material of the inner tube and the outer tube may be the same or may be different. The material which can be fixed easily is preferably selected in the process of fixing an inner tube and an outer tube as a material of an inner tube and an outer tube. The inner diameter of the outer tube is preferably larger than the outer diameter of the inner tube so that the inner tube can be placed in the lumen thereof. This facilitates the work of placing the outer tube over the inner tube. The tubular member 104 may have a plurality of layers above or below the supporting member. The size and hardness of the in-vivo indwelling tube 1 can be controlled by controlling the thickness and material of each layer.

The stacked inner tube and outer tube are fixed. When the inner tube or the outer tube is formed of a thermoplastic material, a heat-shrinkable tube is placed over the inner tube and the outer tube, and the inner tube and the outer tube are fixed by heating and thermal welding. An adhesive may be injected between the inner tube and the outer tube to fix the tubes.

A cut is formed at a predetermined position of the tubular member 104 including the fixed inner tube and outer tube using a cutting means to form a flap portion. The cutting means is preferably a cutter capable of thinly slicing the tubular member 104. The flap portion can be formed, for example, by scraping off the tubular member 104 with a cutter such as a knife, forming a cut in the tubular member 104 with scissors and the like. The position of the flap portion can be formed at a predetermined position of the tubular member 104 in relation to the supporting member.

The production method described above can be applied to the distal side supporting member and the proximal side supporting member. When producing the in-vivo indwelling tube 1 in which the supporting member is provided on the base end side of the midpoint between the base end of the flap and the end portion of the tubular member 104, the thickness of the inner tube is made thicker than the thickness of the outer tube, and the thickness of the flap is made thicker than the outer tube to improve the tear resistance of the flap and to increase the strength of the flap.

As described above, the in-vivo indwelling tube according to the present invention includes a tubular member having a proximal side and a distal side, a proximal flap on the proximal side of the tubular member, the proximal flap having a base end on the proximal side and a free end on a distal side, and a distal flap on the distal side of the tubular member, the distal flap having a base end on the distal side and a free end on the proximal side, where the tubular member includes, radially outward of the tubular member, at least either a distal side first supporting member provided on the distal side of the midpoint between the base end and the free end of the distal flap or a proximal side first supporting member provided on the proximal side of the midpoint between the base end and the free end of the proximal flap. With such a configuration, the strength of at least either the distal flap or the proximal flap can be increased while maintaining the flexibility of the in-vivo indwelling tube itself.

The present application claims the benefit of priority based on Japanese patent application number 2017-115570 filed on Jun. 13, 2017. The entire content of the specification of Japanese patent application number 2017-115570 filed on Jun. 13, 2017 is incorporated herein by reference.

EXAMPLES

Hereinafter, the present invention will be more specifically described with reference to examples, but the present invention is not limited by the following examples as a matter of course, and modifications can of course be appropriately made within a scope which can conform to the description made above and below, all of which being encompassed within the technical scope of the present invention.

An example of a specific production method of the in-vivo indwelling tube is as follows. High hardness polyurethane (product name: Carbothane PC3572D (manufactured by Lubrizol)), low hardness polyurethane (product name: Carbothane PC3555D (manufactured by Lubrizol)) and barium sulfate were knead at a weight ratio of 30:40:30, and an inner tube (outer diameter: inner diameter=2.30 mm: 1.90 mm) of a tubular member was produced through extrusion molding.

Subsequently, the core material was inserted into the inner tube, a ring marker (outer diameter: inner diameter=2.40 mm: 2.35 mm) made of Pt/Ir, which is a supporting member, was placed over the inner tube, and pressure was applied to the outer periphery of the Pt/Ir ring marker using a ring caulking device manufactured by Blockwise Co. (Model SGL-Standard Force) to attach the Pt/Ir ring marker on the outer surface of the inner tube.

An outer tube (outer diameter: inner diameter=2.65 mm: 2.45 mm) produced with the same material as the inner tube in the tubular member was then placed over the inner tube with the Pt/Ir ring marker which is the supporting member.

The heat-shrinkable tube was placed on the outer tube, and heated at 215° C. for 70 seconds to thermally weld the inner tube and the outer tube. The heat-shrinkable tube and the core material were detached, and a cut was formed using a razor at a predetermined position of the tubular member including the thermally welded inner tube and the outer tube to form a flap.

The in-vivo indwelling tubes according to the example were produced through such a production method. As a comparative example, an in-vivo indwelling tube without a supporting member was produced through processes excluding the process of providing the supporting member. The in-vivo indwelling tubes according to the example and the comparative example were the same size and formed of the same material, and as shown in FIGS. 12 and 13, the flap length L5 was 8 mm, the flap thickness T5 was 0.5 mm, and the outer diameter OD of the in-vivo indwelling tube was 2.5 mm. In the example only, the Pt/Ir ring marker which is the proximal side first supporting member 30 having a length in the long axis direction of the tube of 1.5 mm was provided at a location 1.5 mm (FP1) from the base end 106 of the proximal flap 105 toward the proximal end side of the in-vivo indwelling tube and 4 mm (FP2) from the proximal end 102 of the in-vivo indwelling tube toward the proximal flap 105 side.

The tensile strengths of the flap portion of the in-vivo indwelling tubes according to the example and the comparative example were measured, and the measurements values of the tensile strength were compared. The measuring method of tensile strength will be described using FIG. 14. The test method was as follows.

<Measurement Method of Tensile Strength>

1. A measurement sample 301 (product of the present invention and the comparative product) was immersed in water at 37° C. for 2 hours.

2. As shown in FIG. 14, a flap portion 302 of the measurement sample 301 was disposed on the upper chuck 311 of the tension tester, and the end portion 303 of the measurement sample 301 was disposed on the lower chuck 312 of the tension tester. A water tank 320 filled with water at 37° C. was disposed around the chuck portion of a tension tester (Strograph E II-L05 manufactured by TOYOSEIKI). The inter-chuck distance D1, which is the distance between the upper chuck 311 and the lower chuck 312 of the tension tester, was 25 mm.

3. The upper chuck 311 was moved upward at a speed of 500 mm/min, and the maximum load until the measurement sample 301 was broken was taken as the measurement value.

The evaluation results of the tensile test are shown in FIG. 15. The maximum load when the measurement sample 301 of the example was broken was 7.42N, and that of the measurement sample 301 of the comparative example was 6.56N. Thus, it was confirmed that the tensile strength of the flap of the in-vivo indwelling tube in which the supporting member 304 is provided on the base end side of the midpoint between the base end of the flap and the end portion of the tubular member enhances.

DESCRIPTION OF REFERENCE SIGNS

1: in-vivo indwelling tube
2: delivery system
3: inner catheter
4: outer catheter
5: suture thread
6: insertion auxiliary tube
10: distal side first supporting member
10a: proximal end of distal side first supporting member
10b: distal end of the distal side first supporting member
20: distal side second supporting member
20a: proximal end of distal side second supporting member
20b: distal end of distal side second supporting member
30: proximal side first supporting member
30a: proximal end of proximal side first supporting member
30b: distal end of proximal side first supporting member
40: proximal side second supporting member
40a: proximal end of proximal side second supporting member
40b: distal end of proximal side second supporting member
50: first region
50a: proximal end of first region
50b: distal end of first region
60: second region
102: proximal end of in-vivo indwelling tube
103: distal end of in-vivo indwelling tube
104: tubular member
105: proximal flap
106: base end of proximal flap
107: free end of proximal flap
108: distal flap
109: base end of distal flap
110: free end of distal flap
111: larger diameter portion
112: proximal end of larger diameter portion
113: distal end of larger diameter portion
114: smaller diameter portion
115: proximal end of smaller diameter portion
116: distal end of smaller diameter portion
201: conventional in-vivo indwelling tube
202: proximal end of conventional in-vivo indwelling tube
203: distal end of conventional in-vivo indwelling tube
204: conventional tubular member
205: conventional proximal flap
206: base end of conventional proximal flap
207: free end of conventional proximal flap
208: conventional distal flap
209: base end of conventional distal flap
210: free end of conventional distal flap
214: conventional smaller diameter portion
215: proximal end of conventional smaller diameter portion
216: distal end of conventional smaller diameter portion
301: measurement sample
302: flap portion
303: end portion of measurement sample
304: supporting member
311: upper chuck of tension tester
312: lower chuck of tension tester
320: water tank
P1: position of tubular member corresponding to free end of distal flap
P2: position of tubular member corresponding to free end of proximal flap
P3: midpoint between base end and free end of distal flap P4: midpoint between base end and free end of proximal flap P5: midpoint between base end of distal flap and distal end of tubular member P6: midpoint between base end of proximal flap and proximal end of tubular member P7: midpoint between proximal end of distal side first supporting member and distal end of distal side second supporting member P8: midpoint between distal end of proximal side first supporting member and proximal end of proximal side second supporting member P9: midpoint of tubular member D1: inter-chuck distance of tension tester L5: length of flap T5: thickness of flap OD: outer diameter of in-vivo indwelling tube FP1: distance from base end of proximal flap to proximal end side of in-vivo indwelling tube FP2: distance from proximal end of in-vivo indwelling tube to proximal flap side

The invention claimed is:

1. An in-vivo indwelling tube comprising:
   a tubular member having a proximal side and a distal side;
   a proximal flap, having a base end on a proximal side and a free end on a distal side, on the proximal side of the tubular member;
   a distal flap, having a base end on a distal side and a free end on a proximal side, on the distal side of the tubular member; and
   at least one of a distal side first supporting member and a proximal side first supporting member, wherein
   the distal side first supporting member is provided on a distal side of a midpoint between the base end and the free end of the distal flap, or
   the proximal side first supporting member is provided on a proximal side of a midpoint between the base end and the free end of the proximal flap, and
   the distal side first supporting member and the proximal side first supporting member are tubular, and the inner diameter of the distal side first supporting member and the inner diameter of the proximal side first supporting member are smaller than the outer diameter of the tubular member.

2. The in-vivo indwelling tube according to claim 1, wherein
   the distal side first supporting member is provided on the proximal side of the base end of the distal flap, or
   the proximal side first supporting member is provided on the distal side of the base end of the proximal flap.

3. The in-vivo indwelling tube according to claim 1, wherein
   the distal side first supporting member is provided over the base end of the distal flap, or
   the proximal side first supporting member is provided over the base end of the proximal flap.

4. The in-vivo indwelling tube according to claim 1, wherein
   the distal side first supporting member is provided on a proximal side of a midpoint between the base end of the distal flap and the distal end of the tubular member, or
   the proximal side first supporting member is provided on the distal side of a midpoint between the base end of the proximal flap and the proximal end of the tubular member.

5. The in-vivo indwelling tube according to claim 1, further comprising at least one of a distal side second supporting member and a proximal side second supporting member, wherein
   the distal side second supporting member is provided on the proximal side of the free end of the distal flap and on the distal side of a midpoint of the tubular member, or
   the proximal side second supporting member is provided on the distal side of the free end of the proximal flap and on the proximal side of a midpoint of the tubular member.

6. The in-vivo indwelling tube according to claim 5, wherein
   a midpoint between the proximal end of the distal side first supporting member and the distal end of the distal side second supporting member is on the distal side of the free end of the distal flap, and
   a midpoint between the distal end of the proximal side first supporting member and the proximal end of the proximal side second supporting member is on the proximal side of the free end of the proximal flap.

7. The in-vivo indwelling tube according to claim 1, wherein the tubular member includes a first region and a second region sequentially from the proximal side of the tubular member, and a color of the first region and a color of the second region differ from each other on the distal side of the base end of the proximal flap.

8. The in-vivo indwelling tube according to claim 5, wherein
   the tubular member includes a first region and a second region sequentially from the proximal side of the tubular member,
   the tubular member includes a larger diameter portion having a maximum outer diameter larger than an average outer diameter of the tubular member between a position of the tubular member corresponding to the free end of the distal flap or the proximal end of the distal side second supporting member, and a position of the tubular member corresponding to the free end of the proximal flap or the distal end of the first region, and
   the larger diameter portion on at least either the proximal side of the base end of the proximal flap or the distal side of the base end of the distal flap.

9. The in-vivo indwelling tube according to claim 5, wherein
   the tubular member includes a first region and a second region sequentially from the proximal side of the tubular member,
   the tubular member includes a smaller diameter portion having a minimum outer diameter smaller than an average outer diameter of the tubular member between the position of the tubular member corresponding to the free end of the distal flap or the proximal end of the distal side second supporting member, and the position of the tubular member corresponding to the free end of the proximal flap or the distal end of the first region, and
   the smaller diameter portion is on at least either between the base end of the proximal flap and the position on the proximal side of the free end of the proximal flap when the proximal flap is in a closed state or between the base end of the distal flap and a position on the distal side of the free end of the distal flap when the distal flap is in a closed state.

10. The in-vivo indwelling tube according to claim 9, wherein the tubular member has a hole in the smaller diameter portion.

11. The in-vivo indwelling tube according to claim 1, wherein
the tubular member includes at least one supporting member of the distal side first supporting member, a distal side second supporting member provided on the proximal side of the free end of the distal flap and on the distal side of a midpoint of the tubular member, the proximal side first supporting member, and a proximal side second supporting member provided on the distal side of the free end of the proximal flap and on the proximal side of a midpoint of the tubular member, and the shape of the at least one supporting member is tubular.

12. The in-vivo indwelling tube according to claim 1, wherein
the tubular member includes at least one supporting member of the distal side first supporting member, a distal side second supporting member provided on the proximal side of the free end of the distal flap and on the distal side of a midpoint of the tubular member, the proximal side first supporting member, and a proximal side second supporting member provided on the distal side of the free end of the proximal flap and on the proximal side of a midpoint of the tubular member, and the inner diameter of the at least one supporting member is smaller than the outer diameter of the tubular member.

13. The in-vivo indwelling tube according to claim 1, wherein
the tubular member includes at least one supporting member of the distal side first supporting member, a distal side second supporting member provided on the proximal side of the free end of the distal flap and on the distal side of a midpoint of the tubular member, the proximal side first supporting member, and a proximal side second supporting member provided on the distal side of the free end of the proximal flap and on the proximal side of a midpoint of the tubular member, and
the material that constitutes the at least one supporting member is metal, or resin in which a type A durometer hardness of the material that constitutes the at least one supporting member is higher than a type A durometer hardness of the material that constitutes the tubular member.

14. The in-vivo indwelling tube according to claim 1, further comprising a distal side second supporting member when the in-vivo indwelling tube comprising the distal side first supporting member, wherein
the distal side second supporting member is provided on the proximal side of the free end of the distal flap and on the distal side of a midpoint of the tubular member.

15. The in-vivo indwelling tube according to claim 1, further comprising a proximal side second supporting member when the in-vivo indwelling tube comprising the proximal side first supporting member, wherein
the proximal side second supporting member is provided on the distal side of the free end of the proximal flap and on the proximal side of a midpoint of the tubular member.

* * * * *